United States Patent
Ali et al.

(10) Patent No.: US 10,385,687 B2
(45) Date of Patent: Aug. 20, 2019

(54) DETERMINING THE IMMINENT ROCK FAILURE STATE FOR IMPROVING MULTI-STAGE TRIAXIAL COMPRESSION TESTS

(71) Applicant: Baker Hughes, a GE company, LLC, Houston, TX (US)

(72) Inventors: Syed Shujath Ali, Al-Khobar (SA); Ali Al Dhamen, Qatif (SA); Guodong Jin, Katy, TX (US)

(73) Assignee: Baker Hughes, a GE company, LLC, Houston, TX (US)

( * ) Notice: Subject to any disclaimer, the term of this patent is extended or adjusted under 35 U.S.C. 154(b) by 0 days.

(21) Appl. No.: 15/804,505

(22) Filed: Nov. 6, 2017

(65) Prior Publication Data

US 2018/0058212 A1 Mar. 1, 2018

Related U.S. Application Data

(63) Continuation-in-part of application No. 15/343,824, filed on Nov. 4, 2016.
(Continued)

(51) Int. Cl.
*E21B 49/02* (2006.01)
*E21B 25/00* (2006.01)
(Continued)

(52) U.S. Cl.
CPC .............. *E21B 49/02* (2013.01); *E21B 25/00* (2013.01); *G01N 3/08* (2013.01); *G01N 33/24* (2013.01);
(Continued)

(58) Field of Classification Search
CPC ............ G01N 3/08; E21B 25/00; E21B 49/02
(Continued)

(56) References Cited

U.S. PATENT DOCUMENTS

| | | | | |
|---|---|---|---|---|
| 3,673,861 A | * | 7/1972 | Handy | E02D 1/022 |
| | | | | 73/784 |
| 3,907,034 A | * | 9/1975 | Suman, Jr. | E21B 21/08 |
| | | | | 175/50 |

(Continued)

FOREIGN PATENT DOCUMENTS

WO 2014205248 A2 12/2014

OTHER PUBLICATIONS

Taheri et al. (Taheri, Abbas & Tani, Kazuo, (2008), Proposal of a new multiple-step loading triaxial compression testing method).*
(Continued)

*Primary Examiner* — Nathaniel T Woodward
(74) *Attorney, Agent, or Firm* — Mossman, Kumar & Tyler, P.C.

(57) ABSTRACT

Methods and apparatus for evaluation of an earth formation including evaluating a core sample obtained from the formation. Methods include using a change in measurements of at least one stress parameter of the core sample, such as radial strain, axial stress, and acoustic emission counts, over time responsive to an applied stress to estimate imminent rock failure in the core sample. This may include estimating the imminent rock failure using differences between portions of a curve generated based on the measurements. A method employing calculating a rate of change between a plurality of measurements of at least one stress parameter of the core sample over time responsive to an applied stress; and determining a point of imminent failure using the rate of change in the plurality of measurements of the at least one stress parameter is also included.

7 Claims, 24 Drawing Sheets

Related U.S. Application Data

(60) Provisional application No. 62/252,220, filed on Nov. 6, 2015.

(51) Int. Cl.
*G01N 33/24* (2006.01)
*G01N 3/08* (2006.01)

(52) U.S. Cl.
CPC .............. *G01N 2203/0218* (2013.01); *G01N 2203/0284* (2013.01)

(58) Field of Classification Search
USPC ......................................................... 73/818
See application file for complete search history.

(56) References Cited

U.S. PATENT DOCUMENTS

| | | | | |
|---|---|---|---|---|
| 5,226,310 | A | * | 7/1993 | Steiger .................. E21B 49/006 73/38 |
| 5,253,518 | A | * | 10/1993 | Steiger .................. E21B 49/006 166/250.01 |
| 5,619,475 | A | * | 4/1997 | Winkler ................... G01H 5/00 181/105 |
| 2006/0131074 | A1 | * | 6/2006 | Calhoun ............... E21B 49/006 175/50 |
| 2009/0132218 | A1 | * | 5/2009 | Ledgerwood, III .... E21B 10/00 703/7 |
| 2009/0164128 | A1 | | 6/2009 | Tchakarov et al. |
| 2010/0051347 | A1 | | 3/2010 | Tchakarov et al. |
| 2011/0094295 | A1 | * | 4/2011 | Meadows ................ G01N 3/08 73/38 |
| 2014/0326073 | A1 | | 11/2014 | Meadows et al. |
| 2015/0152724 | A1 | | 6/2015 | Amendt et al. |

OTHER PUBLICATIONS

International Search Report & Written Opinion in PCT/US2016/060742, dated Feb. 15, 2017.

Jan. 31, 2019 email from Abbas Taheri to Goudong Jin re. Question about secant Young's Modulus definition in your paper 2008.

Taheri, A., et al., "Study on variations of peak strength of a sandstone during cyclic loading," Geomech. Geophys. Geo-energ. Geo-resour., 2016, 1-10.

Taheri, A., et al., "A new multiple-step loading triaxial test method for brittle rocks," Proc. 19th NZGS Geotechnical Symposium, 2013, 1-8.

* cited by examiner

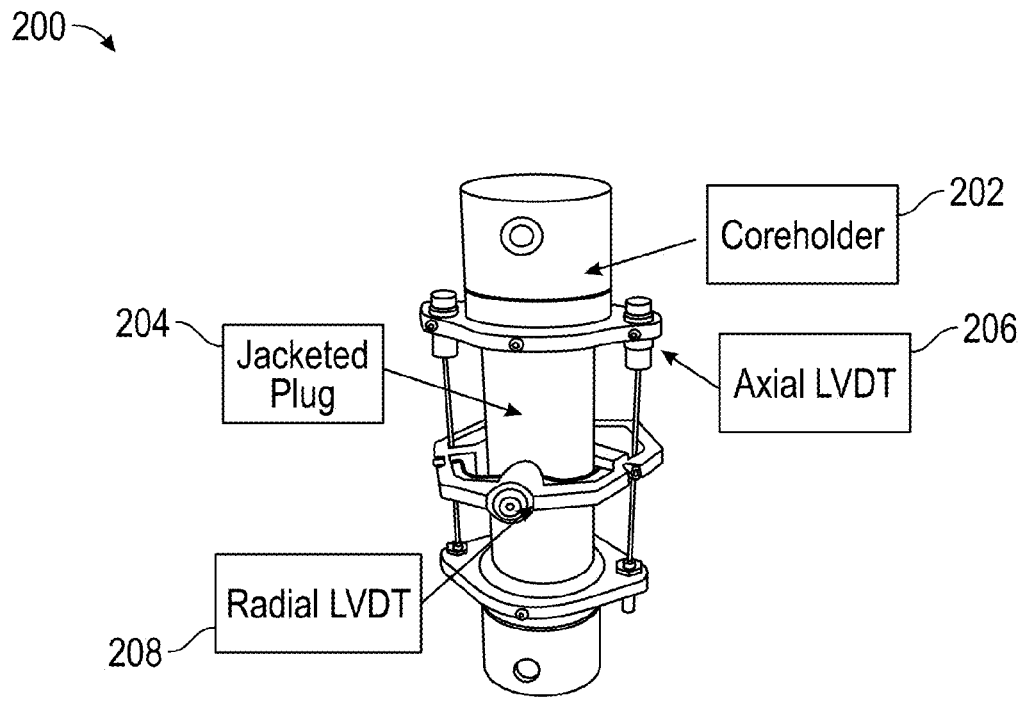
FIG. 3A
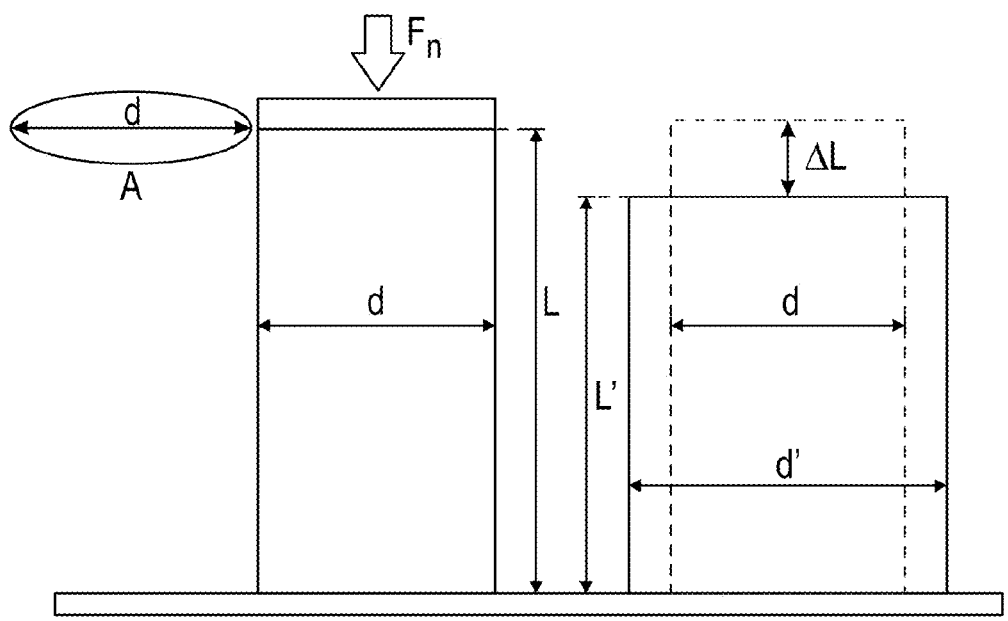
FIG. 3B  FIG. 3C

DETERMINING THE IMMINENT ROCK FAILURE STATE FOR IMPROVING MULTI-STAGE TRIAXIAL COMPRESSION TESTS

CROSS REFERENCE TO RELATED APPLICATIONS

This application is a continuation-in-part of U.S. patent application Ser. No. 15/343,824, filed Nov. 4, 2016 which claims priority from U.S. Provisional Patent Application Ser. No. 62/252,220, filed Nov. 6, 2015, both of which is incorporated herein by reference in their entirety.

FIELD OF THE DISCLOSURE

The present disclosure is related to the field of evaluating a core sample obtained from a subterranean earth formation. More specifically, the present disclosure is related to methods of estimating imminent rock failure of a core sample under mechanical testing.

BACKGROUND OF THE ART

The estimation of mechanical parameters of an earth formation is important for many applications such as reservoir stress-state determination, horizontal drilling and hydraulic fracturing design. These parameters include Young's modulus, Poisson's ratio, cohesion, angle of internal friction, Mohr-Coulomb failure envelope, and unconfined compressive strength. Their determination is commonly performed via core sample analysis, including compression tests of core samples at various confining pressures. Characterizing these parameters facilitates optimization of further operations conducted in the formation, such as fracturing operations, drilling, or other exploration or completion operations of a typical oil or gas well.

SUMMARY OF THE DISCLOSURE

Aspects of the present disclosure relate to evaluation of an earth formation. Other aspects relate to evaluating a core sample obtained in the earth formation.

One general embodiment in accordance with the present disclosure is a method for estimating a property of an earth formation, including associated stresses.

General method embodiments include using a change in measurements of at least one stress parameter of the core sample over time responsive to an applied stress to estimate imminent rock failure in the core sample. This may include estimating the imminent rock failure using differences between portions of a curve generated based on the measurements. The curve may be generated based on the measurements, and may include at least one of: i) radial strain with time; and ii) acoustic emission counts with time.

Methods may include generating a reference line using a first portion of the curve; identifying a second portion of the curve substantially deviating from the reference line. Methods may include using the second portion to generate a second reference line. Methods may include iteratively generating additional reference lines until a stopping condition is met, wherein generating the additional reference lines is carried out by identifying an additional portion of the curve substantially deviating from a most recent reference line and generating an additional reference line from the additional portion. Methods may include estimating the imminent rock failure when the stopping condition is met.

Methods may include causing the applied stress to be ceased upon estimating the imminent rock failure. The at least one stress parameter may be at least one of: i) radial strain; ii) axial stress; and iii) acoustic emission counts. Methods may include using the measurements to determine a Mohr-Coulomb failure envelope for the core sample. Methods may include using the measurements to determine at least one of: i) a parameter of interest of the core sample; and ii) a parameter of interest of the formation. In some implementations, the at least one stress parameter comprises all of: i) radial strain; ii) axial stress; and iii) acoustic emission counts.

The present disclosure also includes apparatus embodiments for estimating a property of an earth formation. The apparatus may include an instrument configured to apply a stress to a core sample obtained in the formation and take measurements of at least one stress parameter of the core sample over time responsive to the applied stress; and at least one processor configured to carry out methods described herein. For example, the processor may be configured to use a change in measurements of the at least one stress parameter of the core sample over time from the instrument responsive to the applied stress to estimate imminent rock failure in the core sample. Configuring the processor may include making a computer readable memory accessible to the processor, wherein the memory comprises a non-transitory computer readable medium having disposed thereon computer program instructions which when executed by the processor cause the performance of the methods described herein.

The apparatus may include a compression testing system. Other apparatus embodiments include various downhole tools. Other method embodiments include producing hydrocarbons from an earth formation.

An additional embodiment is a method A method for evaluating a core sample obtained from a subterranean earth formation, the method comprising: calculating a rate of change between a plurality of measurements of at least one stress parameter of the core sample over time responsive to an applied stress; and determining a point of imminent failure using the rate of change in the plurality of measurements of the at least one stress parameter. This method is quantitative and also allows for the preservation of samples.

BRIEF DESCRIPTION OF THE DRAWINGS

For detailed understanding of the present disclosure, reference should be made to the following detailed description of an exemplary embodiment, taken in conjunction with the accompanying drawing and in which:

FIG. 3A shows an axial load compression device for use with MST testing in accordance with embodiments of the present disclosure.

FIGS. 3B & 3C illustrate the operation of the compression device.

7A-7D plot the variations of the axial stress and the radial strain with respect to time, as well as reference lines tracing the rate of radial strain change.

Figure 8A:
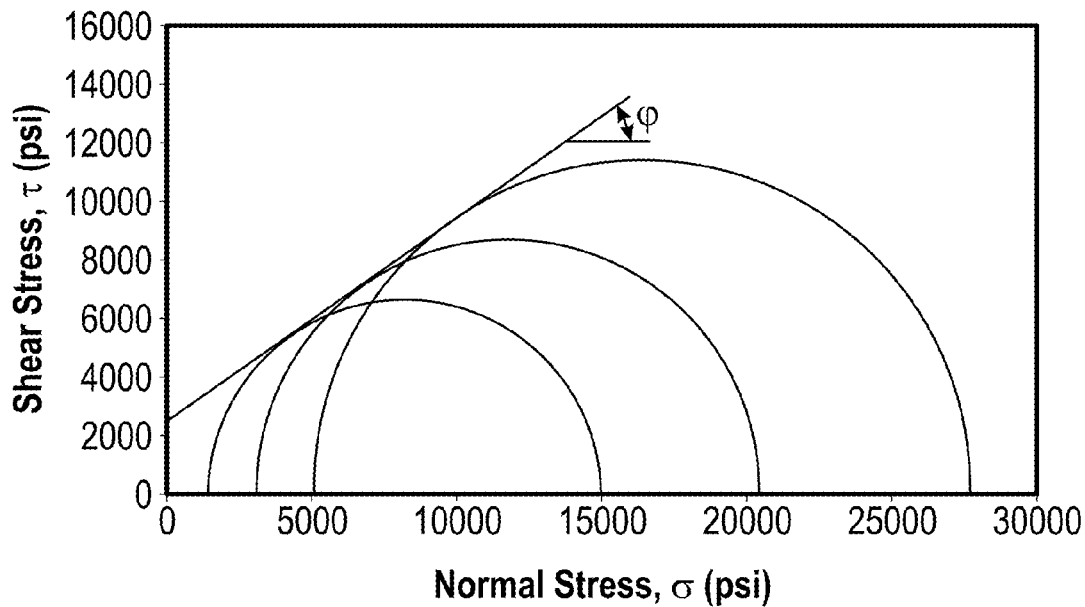
Figure 8B:
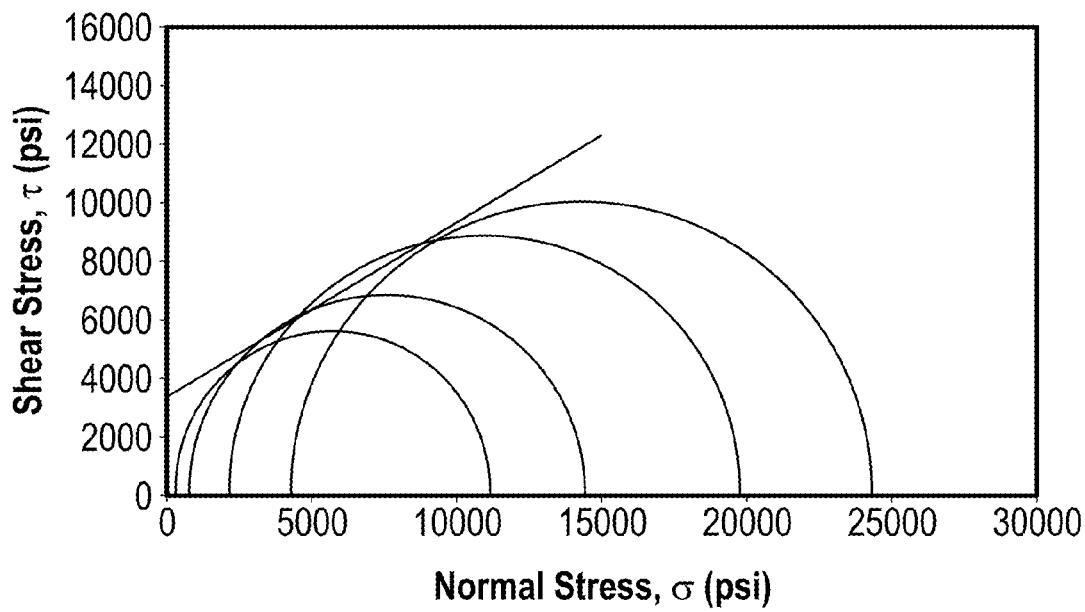
Figure 9A:
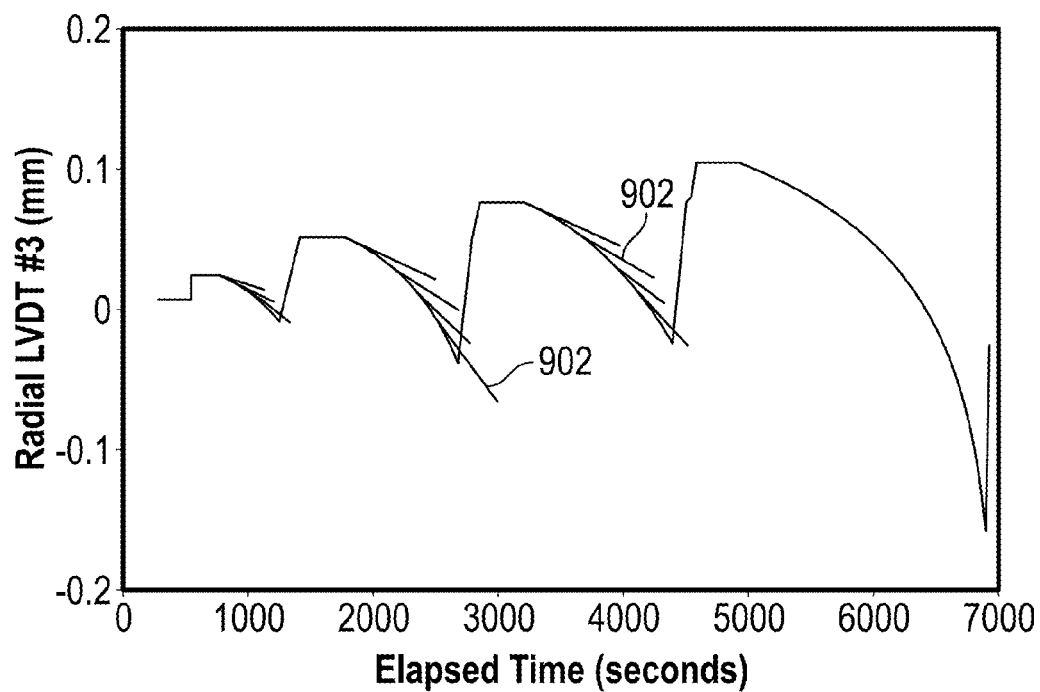
Figure 9B:
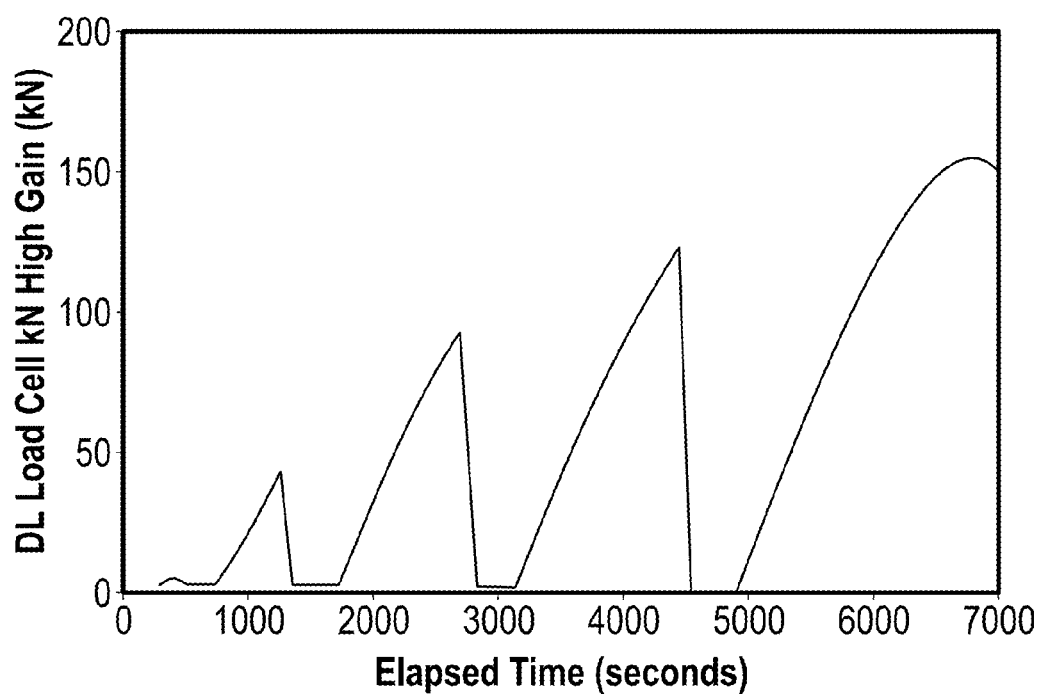
Figure 9C:
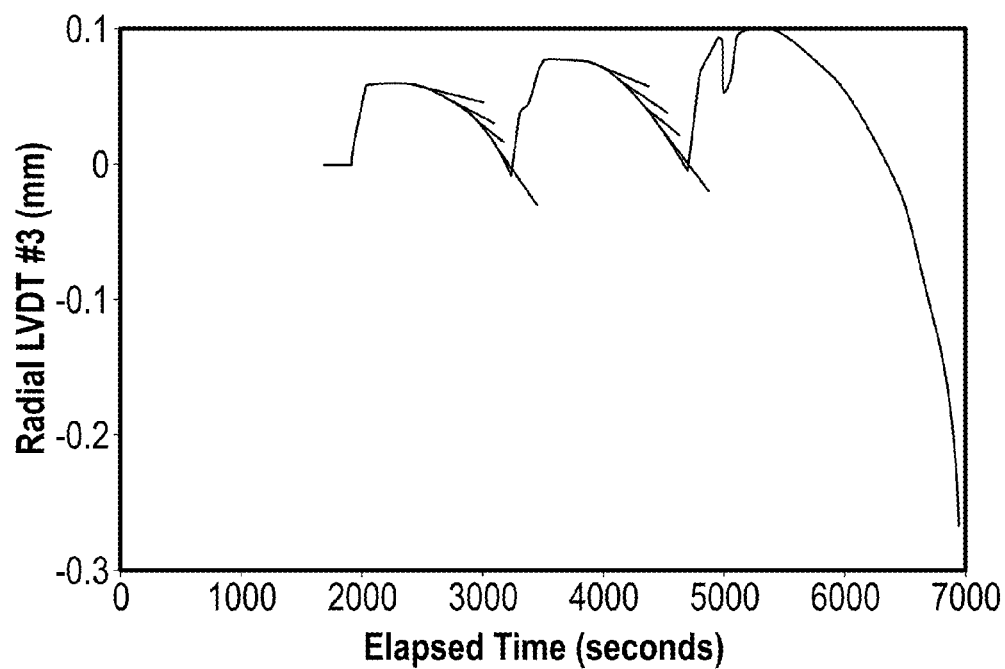
Figure 9D:
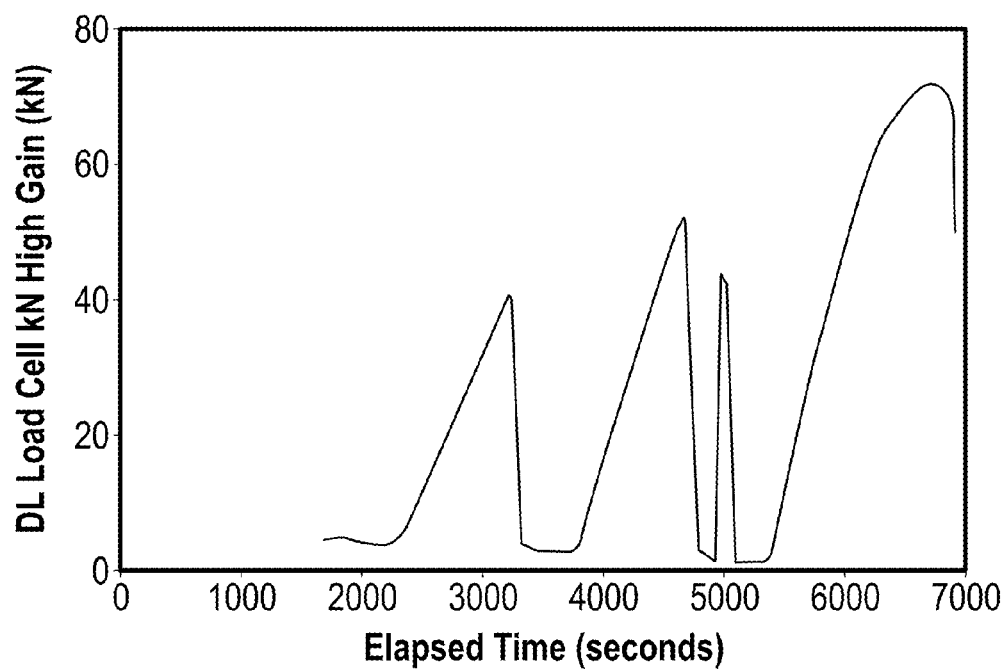

FIGS. 8A & 8B display the Mohr-Coulomb failure envelopes constructed from the measurements of the SST tests described above.

FIGS. 9A-9D show the profiles of radial strain and axial load illustrating results from MST testing of two plugs in accordance with embodiments of the present disclosure.

Figure 10A:
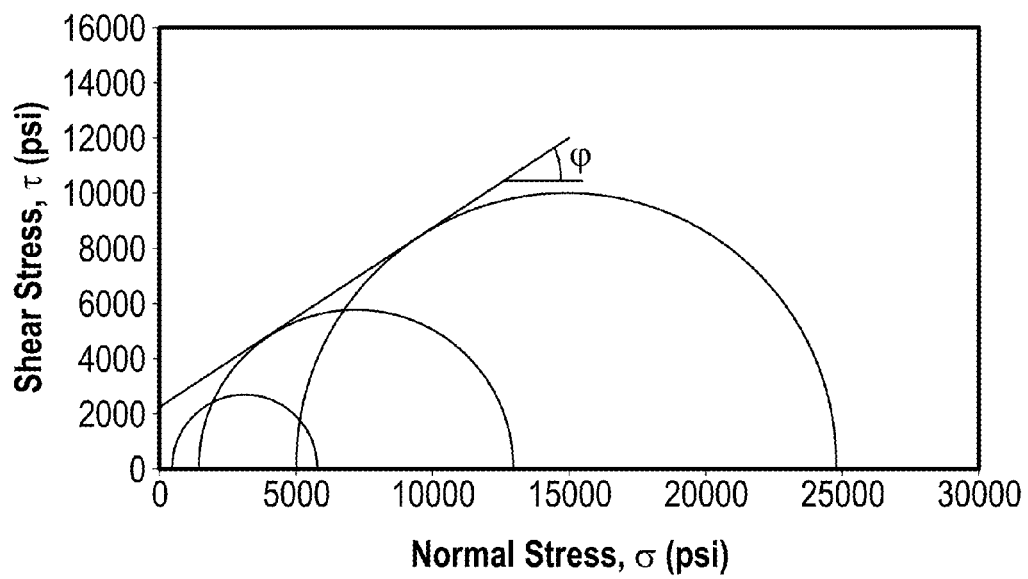
Figure 10B:
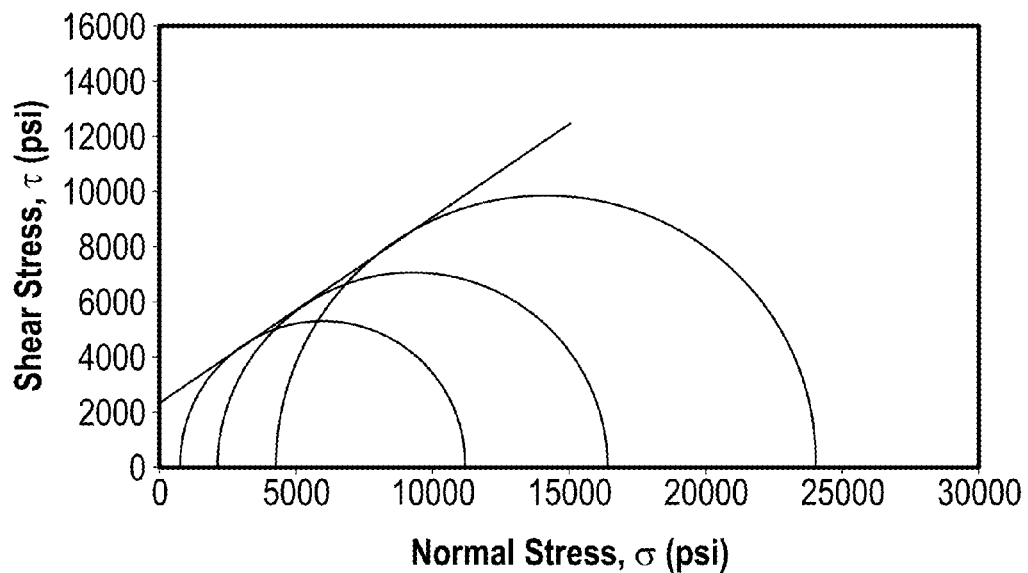

FIGS. 10A & 10B display the Mohr-Coulomb failure envelopes constructed from the measurements of MST tests on Berea sandstone and Mancos shale.

Figure 11A:
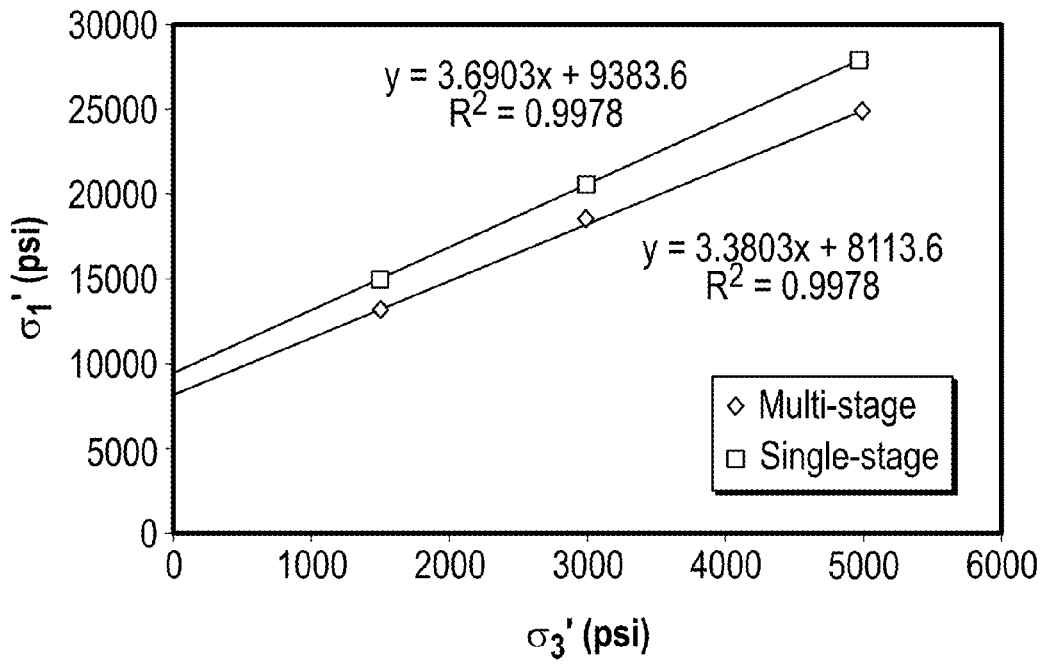
Figure 11B:
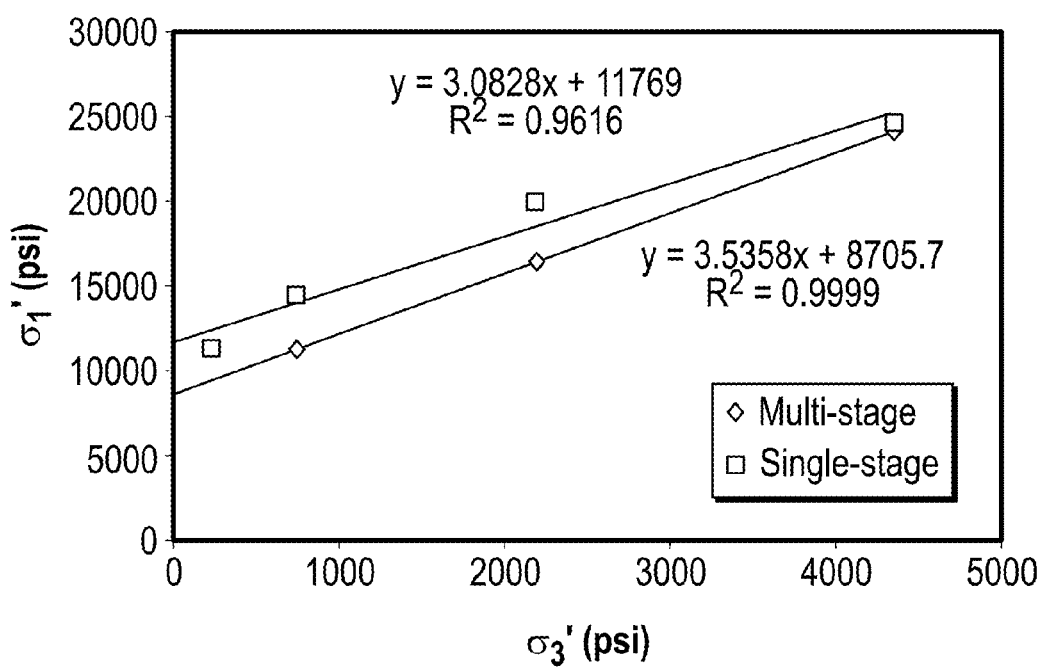

FIGS. 11A-11B compare the Mohr-Coulomb failure envelopes constructed from SST and MST tests.

Figure 12:
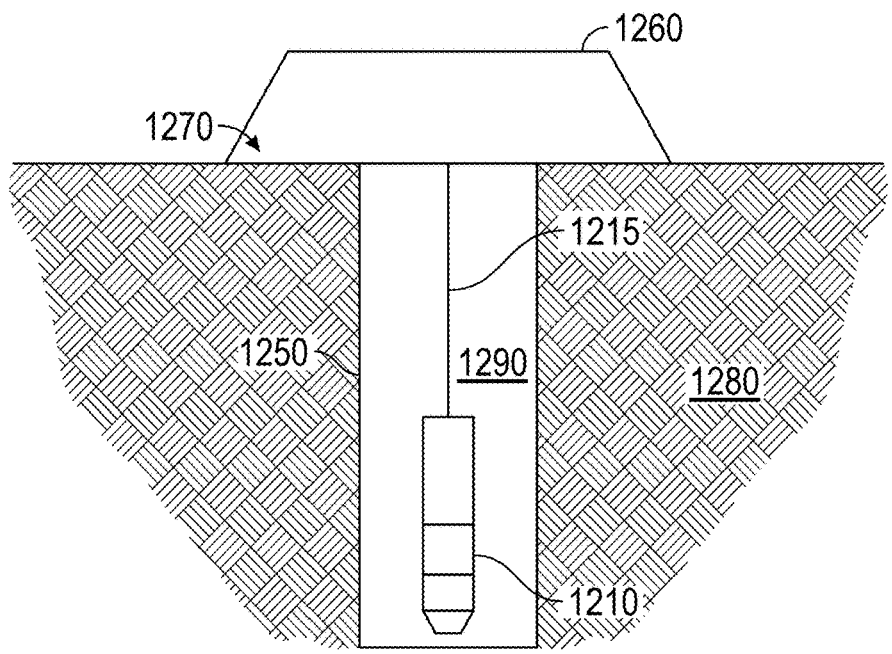

FIG. 12 schematically illustrates a wellbore system having a downhole tool configured to acquire core samples.

Figure 13:
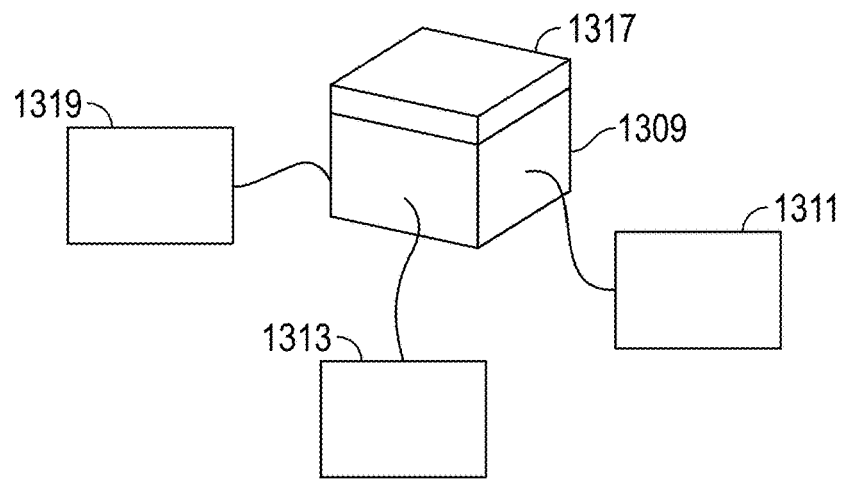

FIG. 13 illustrates a hardware environment in accordance with embodiments of the present disclosure.

Figure 14:
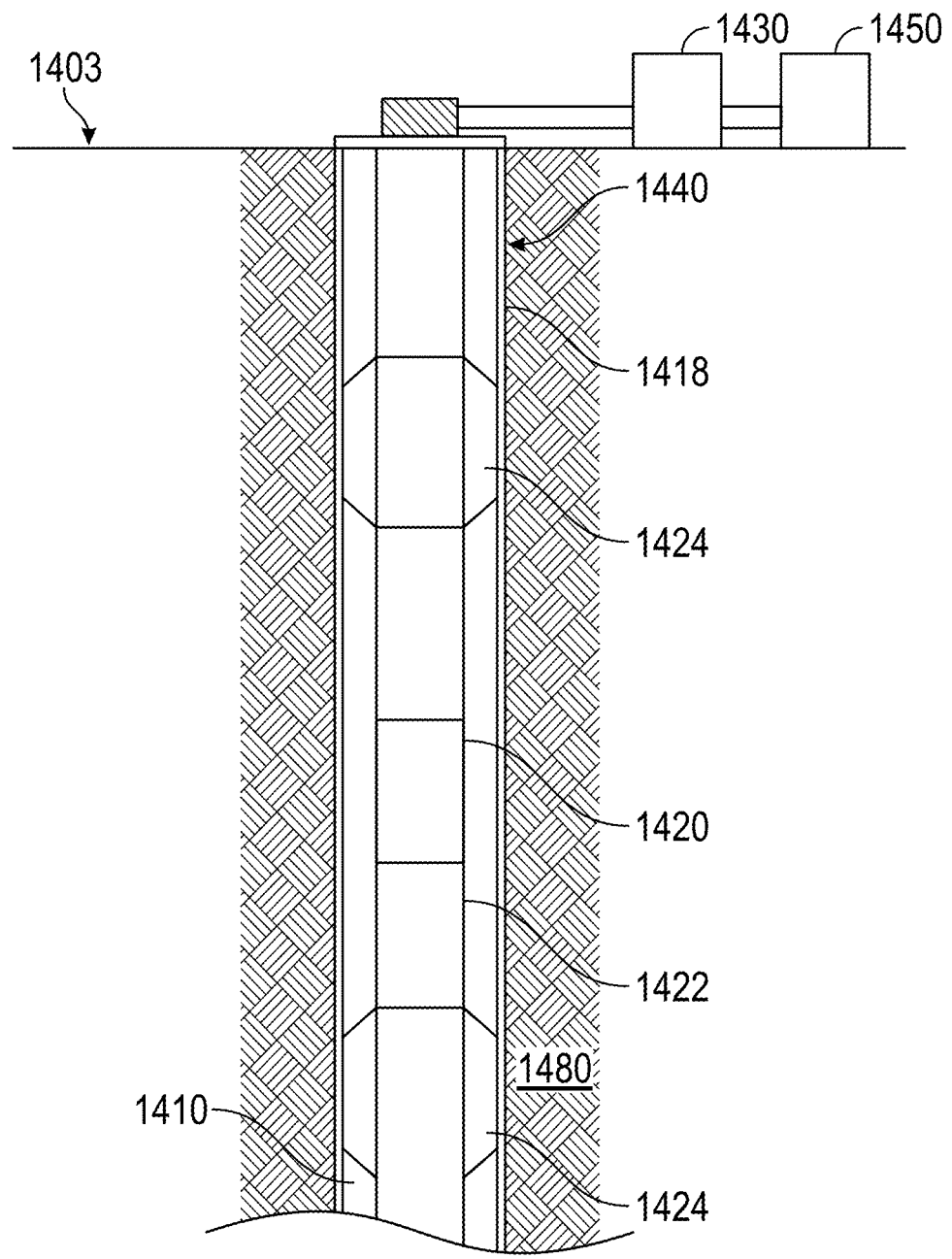

FIG. 14 illustrates a stimulation system in accordance with embodiments of the present disclosure.

Figure 15:
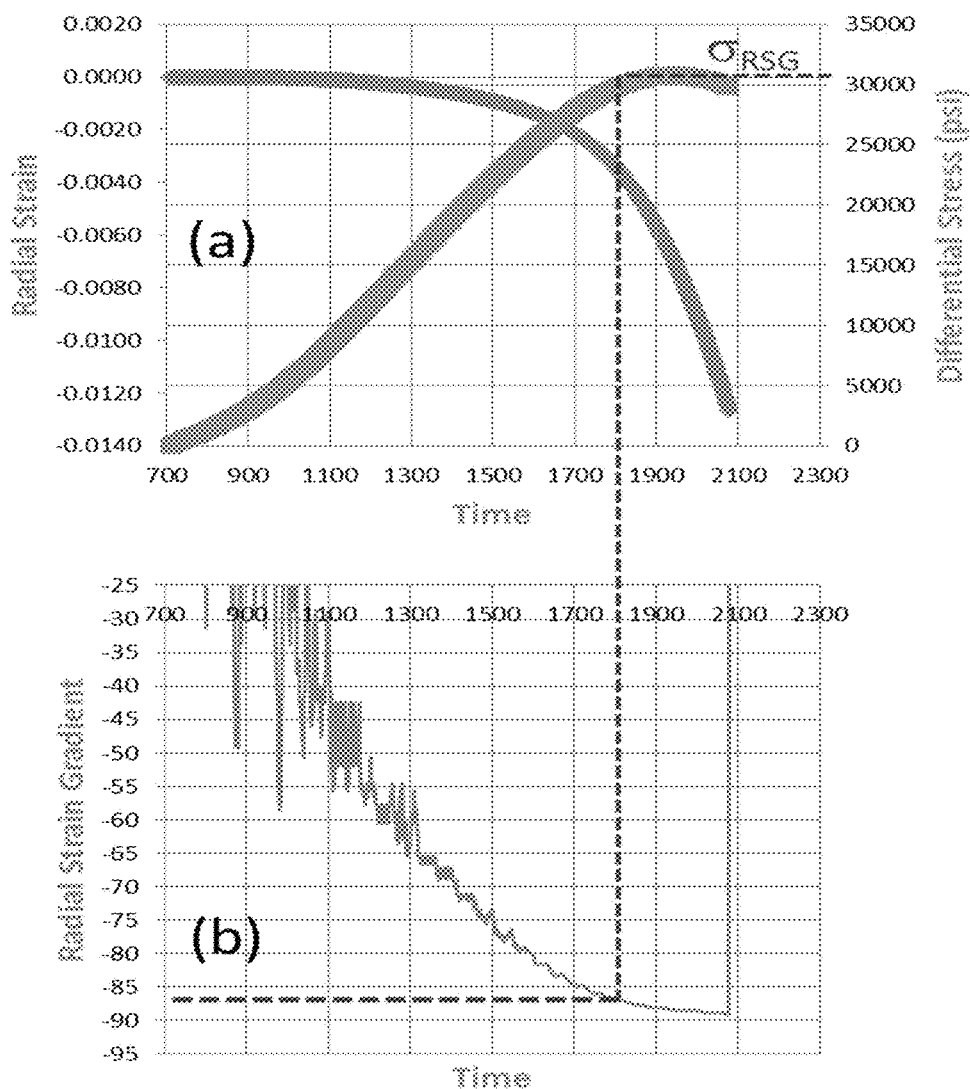

FIG. 15 is a plot showing the use of radial strain gradient to determine imminent rock failure state of a first sample.

Figure 16:
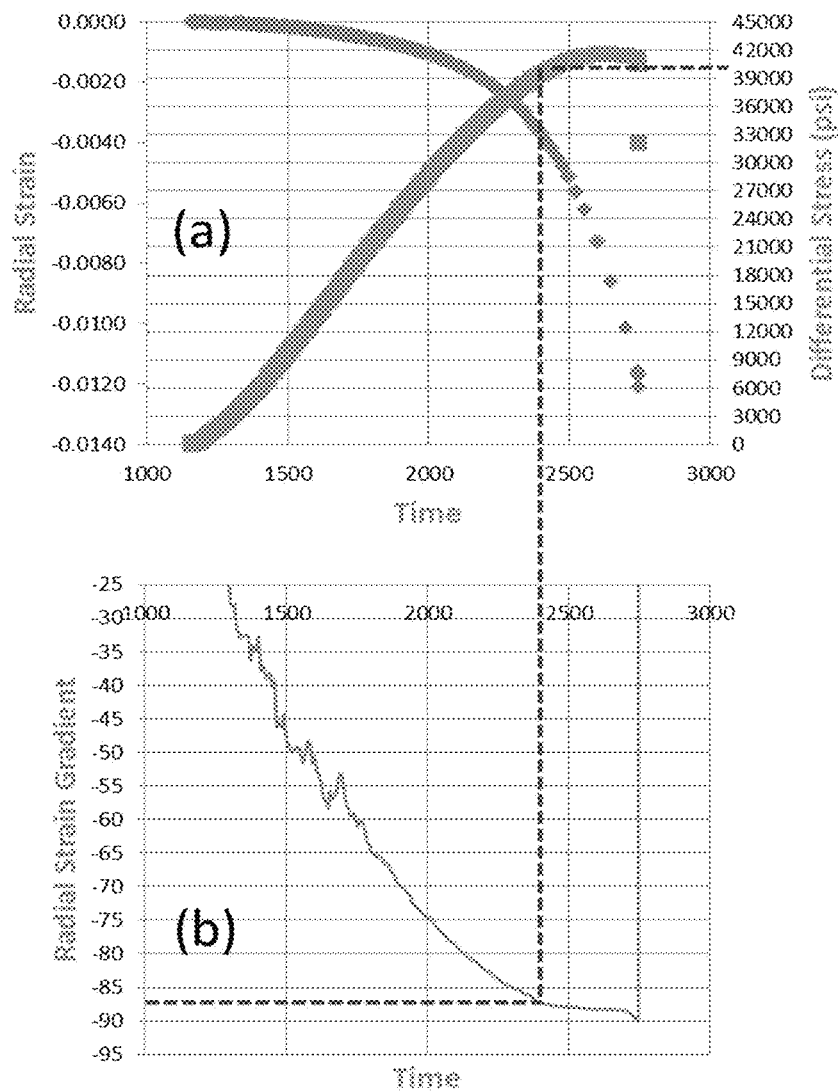

FIG. 16 is a plot showing the use of radial strain gradient to determine imminent rock failure state of a second sample.

Figure 17:
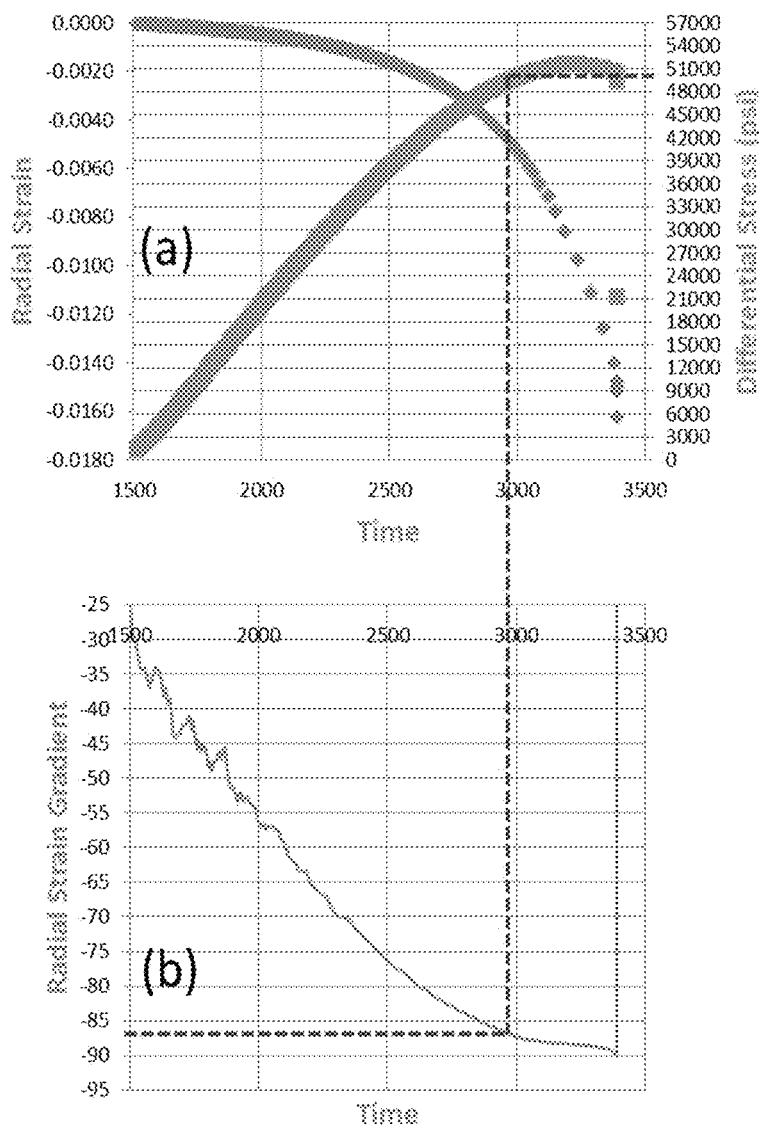

FIG. 17 is a plot showing the use of radial strain gradient to determine imminent rock failure state of a third sample.

DETAILED DESCRIPTION OF THE DISCLOSURE

The present disclosure is discussed with reference to specific instruments. It is to be understood that the choice of the specific instruments discussed herein is not to be construed as a limitation and that the method of the present disclosure may also be used with other instruments.

Aspects of the invention relate to evaluating a core sample obtained from a subterranean earth formation. This may include monitoring stress parameters associated with the core sample being tested while a mechanical stress is applied. These stress parameters (detectable using various appropriate instruments) are responsive to the applied stress and indicative of mechanical properties of the core sample, and by extension the formation. General embodiments include using a change in measurements of a stress parameter of the core sample over time responsive to an applied stress to estimate imminent rock failure in the core sample.

Further aspects of the present disclosure relate to using measurements taken in connection with mechanical testing of the core sample to estimate parameters of interest (e.g., properties of the core sample, the formation, or its constituents), model the formation, and/or predict the behavior of the formation or the wellbore when further operations are conducted on or within it. Example parameters of interest include Young's modulus, Poisson's ratio, cohesion, angle of internal friction, Mohr-Coulomb failure envelope, and unconfined compressive strength. These parameters, models, and predictions (collectively, "formation information") may then be used in performing those further formation operations.

For example, in exploration and development related to hydrocarbon production, it is important to make accurate measurements of geologic formations. The geologic formations below the surface of the earth may contain reservoirs of oil and gas or underground bodies of water. These geologic (earth) formations may include formation layers and various structures. Existing mechanical parameters may impact the design and successful completion of oil and gas and geothermal wells.

For unconventional reservoirs, only a limited number of development techniques may be viable. Multistage hydraulic fracturing on horizontal wells may be necessary, for example, in order to exploit formation reserves in such environments. The accuracy of a Geomechanical Earth Model (GEM) of the basin is desirable, among other reasons, to maintain wellbore stability during drilling of horizontal wells and to optimize hydraulic fracking operations in order to generate the maximum drainage area possible.

Both of these types of operations result in damages to the subsurface rock, which can be detrimental to their respective operational objectives. The precise determination of rock mechanical behavior is therefore of great importance to reduce the uncertainty of GEMs and optimize these operations.

The GEM is a model describing the in-situ stresses and the mechanical parameters of a particular basin or reservoir. These in-situ stresses are constrained with well logs, tests data, and mechanical properties of the formations. The mechanical properties can be divided into elastic and strength parameters. The elastic parameters are defined in two categories: dynamic and the static. The dynamic parameters are obtained from acoustic well logs or ultrasonic tests on core samples in the laboratory, while the static parameters are derived from laboratory experiments on core samples as described below.

The strength parameters are evaluated by destructive laboratory tests on core samples. Determining mechanical parameters (e.g., Young's modulus, Poisson's ratio, cohesion, angle of internal friction, Mohr-Coulomb failure envelope, unconfined compressive strength, etc.) of a core sample is commonly performed via single-stage triaxial (SST) compression tests using three or more core samples at various confining pressures.

Static and strength parameters are very discrete because of the limited rock volume available from whole cores. In contrast, the dynamic properties can be more continuous. There are some practical differences between static and dynamic elastic properties, and no direct correlation exists between dynamic and strength properties.

Estimating these mechanical parameters is important for many oilfield applications, particularly in connection with developing unconventional shale. These mechanical properties are important because the damage on the rock during the drilling and hydraulic fracturing is controlled by these static and strength properties. Many empirical correlations have been proposed between dynamic, static and strength properties of the rock. Most of these correlations are applicable only for conventional reservoir rocks, or rocks with low total organic content ('TOC'), and application to unconventional reservoirs or source rocks is problematic.

Figure 1:
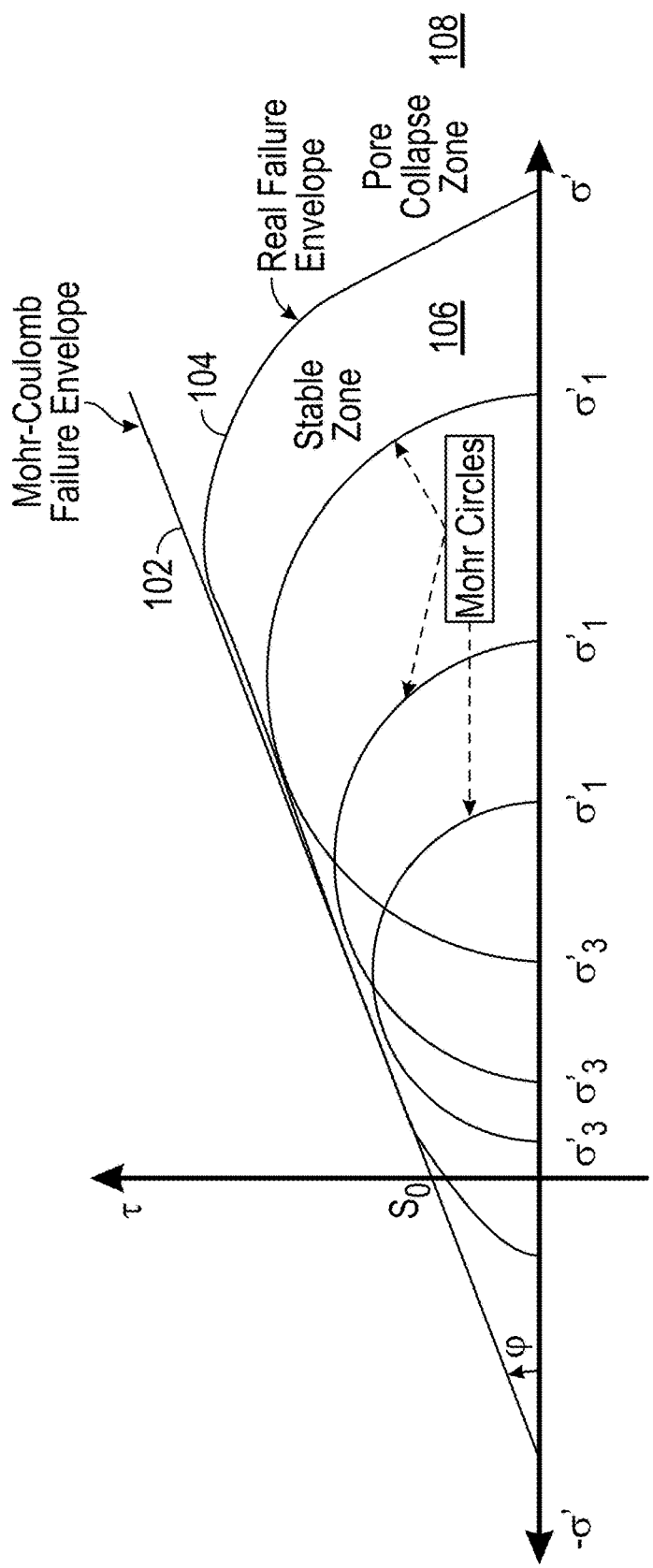
FIG. 1 illustrates an estimated Mohr-Coulomb failure envelope ('MCFE') in accordance with embodiments of the present disclosure.

FIG. 1 illustrates an estimated Mohr-Coulomb failure envelope ('MCFE') in accordance with embodiments of the present disclosure in comparison with an actual failure envelope of a formation. The Mohr-Coulomb failure envelope 102 is a simple but effective mathematical representation of the real failure envelope 104 of a rock. This criterion assumes a lineal function between the shear stress ($\tau$) and normal stress ($\sigma$).

$$|\tau|=S_o+\mu \cdot \sigma \tag{1}$$

$$|\tau|=S_o+\tan(\varphi) \cdot \sigma \tag{2}$$

where $S_o$ is the cohesion or the shear strength of the material at zero normal stress, µ is the internal friction coefficient, for which the internal friction angle φ may be substituted (Eq. 2).

The stable zone 106 is the region of the shear-normal stresses space, where the rock can be deformed elastically or plastically but is still strong enough to support the shear stresses and the normal stresses on the rock. The zone 108 outside the failure envelope curve is where the rock will fail (e.g., will be broken). The real failure envelope 104 of the rock is challenging to describe using an explicit mathematical function.

For practical purposes, the Mohr-Coulomb failure envelope 102, easily modeled as the function of Eq. (1), may be used as an approximation of the real envelope, and is a stress region where most problems in the oil industry are defined. To determine the Mohr-Coulomb failure envelope, at least two triaxial tests should be performed at different confining pressures. Because of the rock heterogeneity, it is highly recommended to carry out three or more triaxial tests at different confining pressures.

Additionally, to generate and validate new correlations for unconventional reservoirs, more geomechanical tests are necessary to be performed on source rocks. In the laboratory, this translates to measuring rock dynamic and static properties on a large number of core plugs with good quality.

For unconventional shale formations, these considerations are a practical bottleneck—it is very difficult to drill multiple plugs with good quality from a whole core because of its brittleness and complexity. Hence, the plugging process is very challenging and the plug recovery is very low, in part due to the weakness of bedding planes. Very few horizontal plugs (parallel to beddings) are recovered that meet the geomechanical requirement for laboratory testing, and even fewer vertical plugs (perpendicular to beddings).

More recently, an alternative to SST, known as multi-stage triaxial (MST) compression testing, which requires only one plug to be tested, has been employed. It was observed that the MST test can generate a reasonable estimation of the failure envelope on ductile materials (e.g. shale samples), but not on brittle rocks such as sandstones. It was later found that the MST method worked well on soil samples; in 1983, MST tests were an established procedure for determining the strength of rock materials in triaxial compression.

MST testing is valuable for the determination of unconventional shale failure envelopes, mainly because of the scarcity of viable shale plugs. It is difficult to obtain enough shale plugs with quality sufficient to carry out conventional SST tests using three samples at three different confining pressures. Often the MST test, which can generate a full failure envelope using a single core plug, is the only workable option.

Figure 2A:
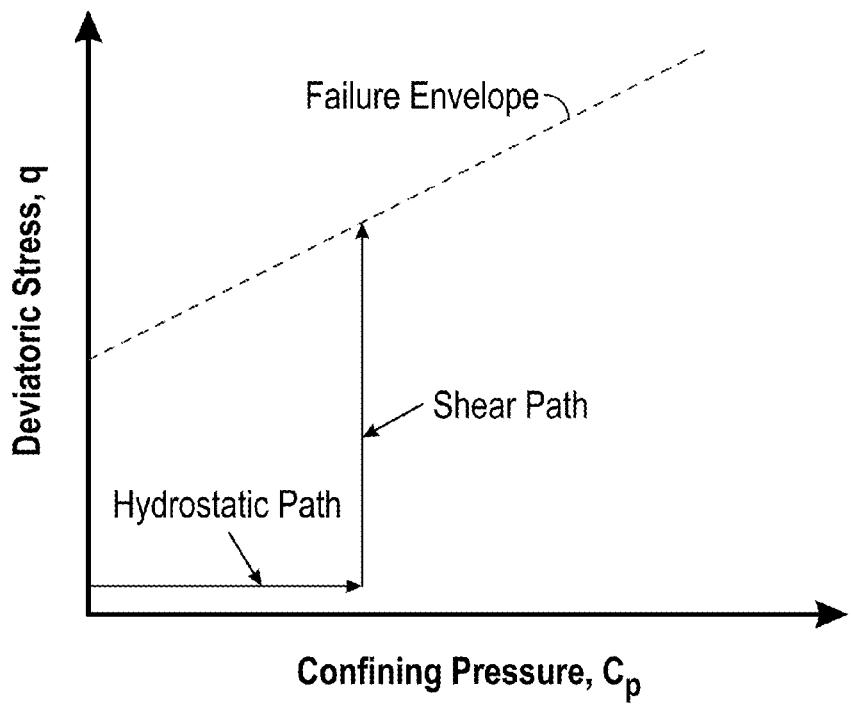
FIGS. 2A-2C display the characteristics of stress paths during SST and MST tests.
Figure 2B:
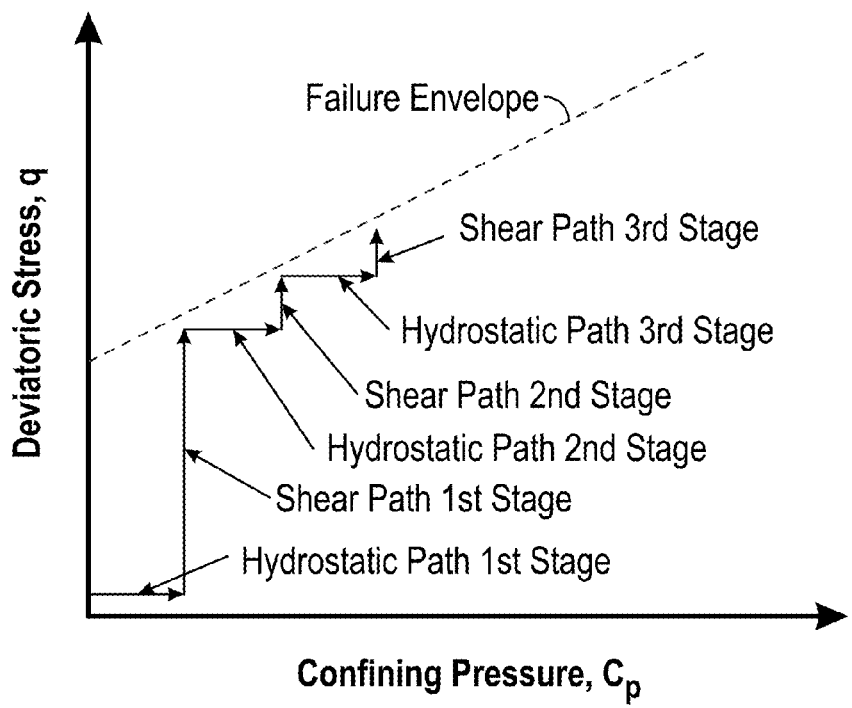
Figure 2C:
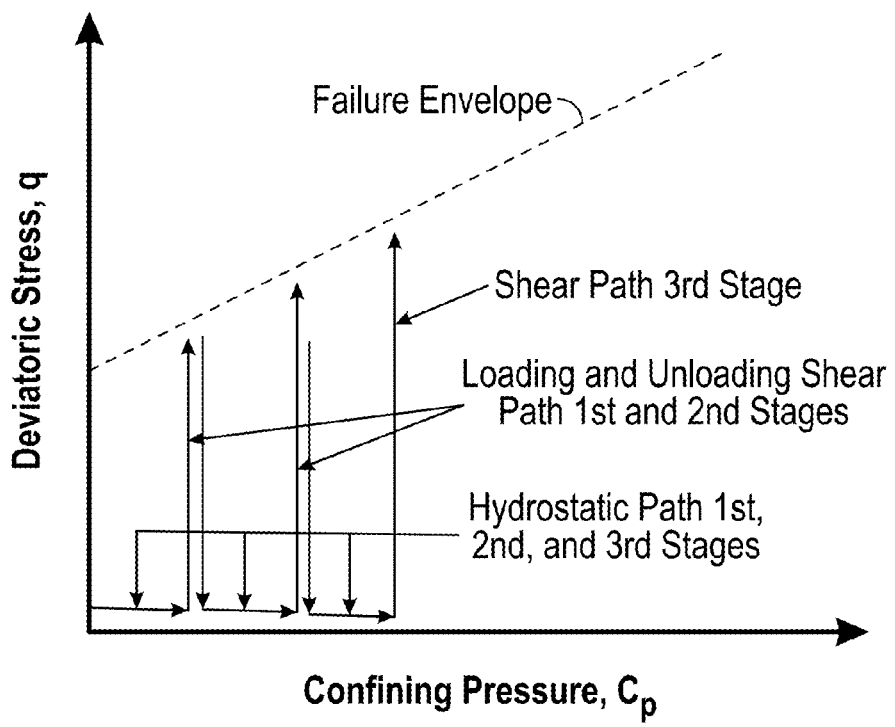

FIGS. 2A-2C display the characteristics of stress paths during the SST and MST tests. In MST, it is critical to cease the application of stresses on the core sample prior to failure (e.g., fracture) of the sample. It is desirable to stop the application of a stress force (e.g., axial load) as close to this failure point as possible. Thus, one objective in performing MST testing is to determine the exact point of stopping the axial load at each stage immediately before this breaking point. This point is referred to as a state of imminent rock failure.

Figure 2D:
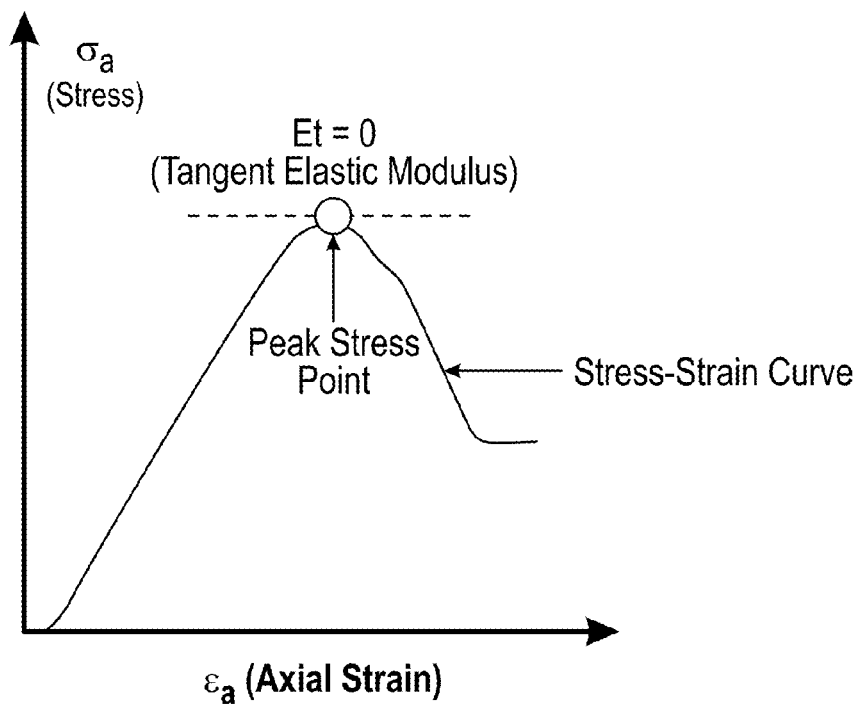
FIG. 2D illustrates characteristics of imminent rock failure.

FIG. 2D illustrates characteristics of imminent rock failure. The imminent failure point may be defined by the region of the stress-axial strain curve where the tangent elastic modulus approaches zero, or by the peak stress point when a core sample fails under compression.

Accurate prediction of stopping points at the first stages of a MST test will affect the usefulness of the test data for the failure envelope calibration. FIG. 2A shows a stress path during a SST test. FIG. 2B shows a stress path characteristic of the original MST tests.

Alternative attempts at estimating imminent rock failure relate to following the stress paths similar to those of a SST test when performing MST testing (FIG. 2C), and used the volumetric strain equal to zero, or alternatively, the maximum volumetric strain, to determine the stopping point at each stage so as to prevent early failures. These methods have been found lacking in reliability.

Later methods operated by following the secant Young's modulus during the test. For example, a radial extensometer may be employed for controlling the axial loading at each stage to improve the prediction of onset of the stopping points.

One challenge of MST testing lies in the practical difficulty of determining the stress-strain state "immediately prior to failure" so as to terminate the test on time at the current stage. That is, it is important to continue testing (applying stress) until the stage immediately prior to failure, without allowing the core sample to fail (e.g., break). An early stop at each stage of the MST test will produce a "conservative" (inaccurate) Mohr-Coulomb failure envelope.

However, using conventional methods, it is not uncommon that an erroneous estimation of the failure state occurs when interpreting these stress-strain curves, as there accurately determining the failure envelope of the sample may be problematic. Judgment must be made regarding the stress-strain state "immediately prior to failure." Thus, the existing methods of performing MST tests fail to provide satisfactory results, such as, for example, accurate estimation of the representative Mohr-Coulomb failure envelope.

Aspects of the disclosure relate to precisely estimating the state of imminent rock failure, which enables more accurate evaluation of the mechanical behavior, the static elastic, and strength parameters with few core plugs.

The present disclosure includes aspects directed to techniques for compression testing which precisely and accurately determine imminent rock failure through continuous monitoring of one or more stress parameters, such as, for example, the radial deformation of the core sample.

Methods of the present disclosure include continuously monitoring one or more stress parameters (e.g., the radial deformation) with time. Variations of the stress parameters are analyzed in accordance with novel techniques described hereinbelow, thus making it possible to timely ascertain the stopping point of each stage so as to avoid an early stop or breaking the plug before the last stage planned for the test. One advantage of methods in accordance with the present disclosure is the ability to obtain a superior calibration of the Mohr-Coulomb failure envelope when only one unconventional core plug is available for the MCS test.

These techniques may be particularly advantageous for MST compression testing. MST methods in accordance with the present disclosure are an efficient procedure to generate the Mohr-Coulomb failure envelope when the availability of core samples with good quality is limited, especially in the exploration and development of unconventional reservoirs.

FIG. 3A shows an axial load compression device for use with MST testing in accordance with embodiments of the present disclosure. The device 200 comprises coreholders 202 at each end of a jacket containing a plug (jacketed plug 204). An axial displacement sensor 206 (e.g., an axial linear variable differential transformer ('LVDT')) and a radial displacement sensor 208 (e.g., a radial LVDT) provide measurements of axial and radial strain or other stress parameters. Aspects of the present disclosure may be applied to any testing system in which the radial strain or deformation can be monitored with any kind of sensors (LVDT, strain gauge, extensometer, and so on).

FIGS. 3B & 3C illustrate the operation of the compression device. FIGS. 3B and 3C illustrate the same sample at different times, and under different forces. FIG. 3B shows the core sample prior to deformation; that is, the core sample in its natural resting state. FIG. 3C shows the core sample under applied stress. When external forces (e.g. Fn) are applied to a cylindrical core sample with a diameter of d and length of L, they produce changes in shape and size of the core sample. Strain is the relative change in shape or size of a core sample due to externally-applied forces. Axial strain is defined as the ratio of variation of sample length ($\Delta L = L - L'$) and the original sample length L; while radial strain is defined as the ratio of variation ($\Delta d = d' - d$) of sample diameter to the original sample diameter (d). Stress is the internal force (per unit area or the like) associated with a strain. Axial stress is defined as the ratio of the externally-applied force (Fn) to the original cross-sectional area of the sample (A).

Figure 4A:
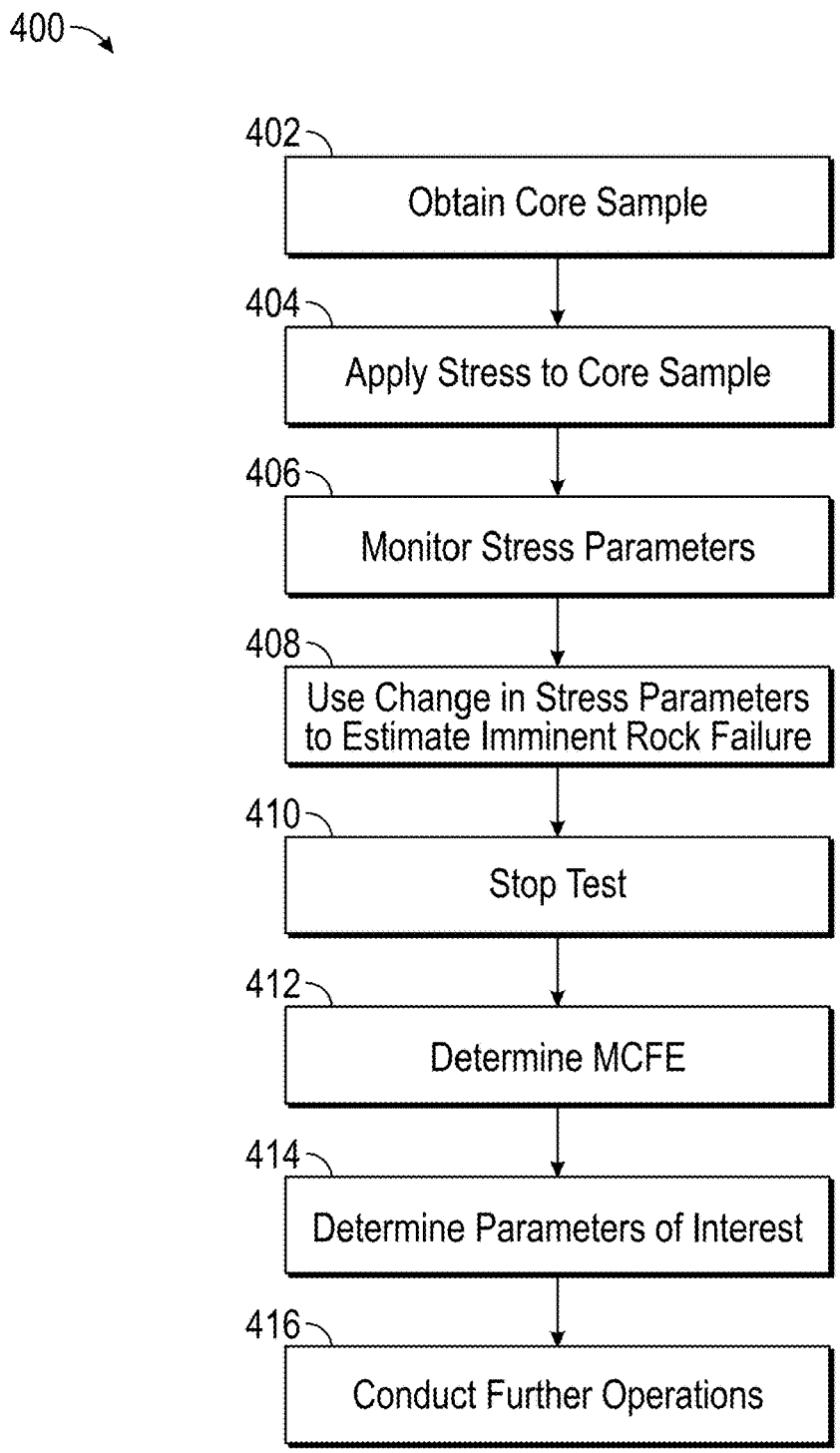
FIGS. 4A & 4B illustrate methods in accordance with embodiments of the present disclosure.

FIG. 4A illustrates a method in accordance with embodiments of the present disclosure. Method 400 is a method for evaluating a core sample obtained from a subterranean earth formation. Method 400 may begin with optional step 402, which includes obtaining the core sample. Optional step 404 comprises applying a stress to a core sample. Any testing system appropriate for core sample strain testing may be used, such as a triaxial compression testing system. The system may be automated and controlled in dependence upon measurement information related to the testing.

Step 406 comprises monitoring one or more stress parameters. For example, variations of radial strain, axial stress, and/or acoustic emission counts may be continuously monitored over time.

Step 408 comprises using a change in measurements of a stress parameter of the core sample over time responsive to the applied stress to estimate imminent rock failure in the core sample. The imminent rock failure may be estimated by detecting a threshold increase in a rate of change in the change in measurements or detecting a threshold rate of increase in a rate of change in the change in measurements. Particular heuristic processes as described below may be used to accurately detect changes signifying imminent rock failure. Step 410 comprises causing applied stress to be ceased upon estimating the imminent rock failure—that is, causing the test to be stopped.

Optional step 412 may include using the measurements to determine a Mohr-Coulomb failure envelope for the core sample. Optional step 414 may include using the measurements to determine at least one of: i) a parameter of interest of the core sample; and ii) a parameter of interest of the formation. Optional step 416 may include using formation information derived from the measurements to conduct further operations in the formation.

Figure 4B:
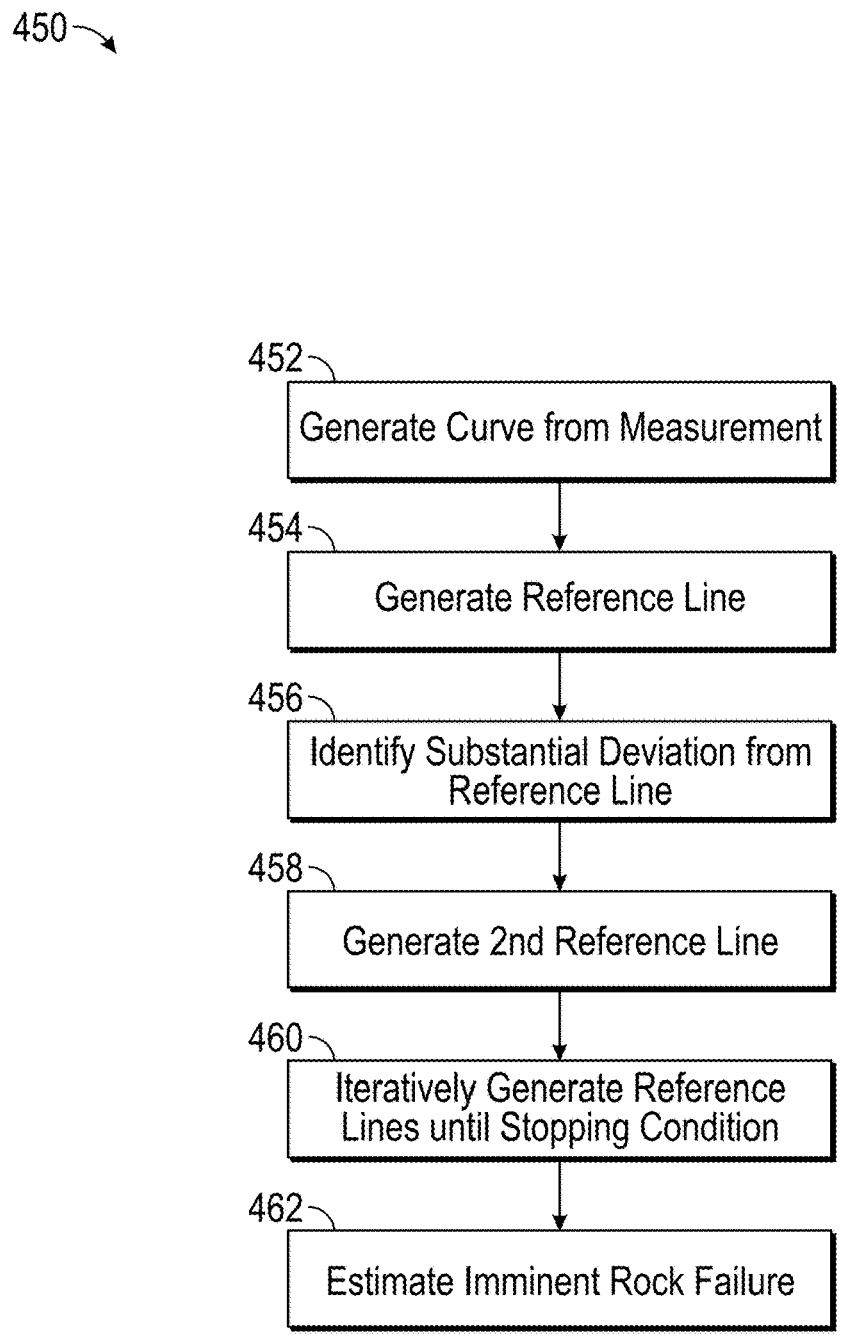

FIG. 4B illustrates a method in accordance with embodiments of the present disclosure. Method 450 is a method for using a change in measurements of a stress parameter of the core sample over time responsive to the applied stress to estimate imminent rock failure in the core sample. Method 450 may include estimating the imminent rock failure using differences between portions of a curve generated based on the measurements. Method 450 may begin with the optional step 452 of generating the curve. This curve may be generated based on the measurements of at least one of: i) radial strain with time; and ii) acoustic emission counts with time. The curve may be a curve of the stress parameter over time, a rate of change of the parameter overtime, and so on.

Step 454 may include generating a reference line using a first portion of the curve. Step 456 may include identifying a second portion of the curve substantially deviating from the reference line. Step 458 may include using this second portion to generate a second reference line. This process may continue at step 460 by iteratively generating additional reference lines until a stopping condition is met. Generating the additional reference lines may include identifying an additional portion of the curve substantially deviating from a most recent reference line; and generating an additional reference line from the additional portion. Reference lines may be a tangent to the curve at a point.

For example, generation of a first reference line may be initiated after a threshold period of time has passed from the start of axial loading, a threshold number of measurement data points have been obtained, or the like. Generating further reference lines may be based on substantial deviation of a measurement or the curve from a preceding (e.g., most current) reference line. The newly generated reference line may start from the point where the curve substantially deviates.

Step 462 may include estimating the imminent rock failure when the stopping condition is met. The stopping condition may be related to comparisons between prior sections of the curve to more recent sections, comparisons between the most recent reference line and later curve section, exceeding a threshold for differences between prior and later curve sections, tangents, reference lines, or combinations of these. In some implementations, a stopping condition may occur when a threshold number of reference lines have been generated. The stopping condition may be selected in accordance with properties of the core sample, the formation, previous measurements, and the like. Different stages of a multistage test may employ different rules and heuristics, including different stopping conditions.

The volumetric strain ($\varepsilon_v$) is one of the parameters used to improve the estimation of imminent rock failure (and thus, the stopping points) at each stage of a MST test. This parameter is not measured directly, but rather calculated. A radial extensometer may be used to control the MST test, which generates the best matching results of the failure envelopes.

Figure 5:
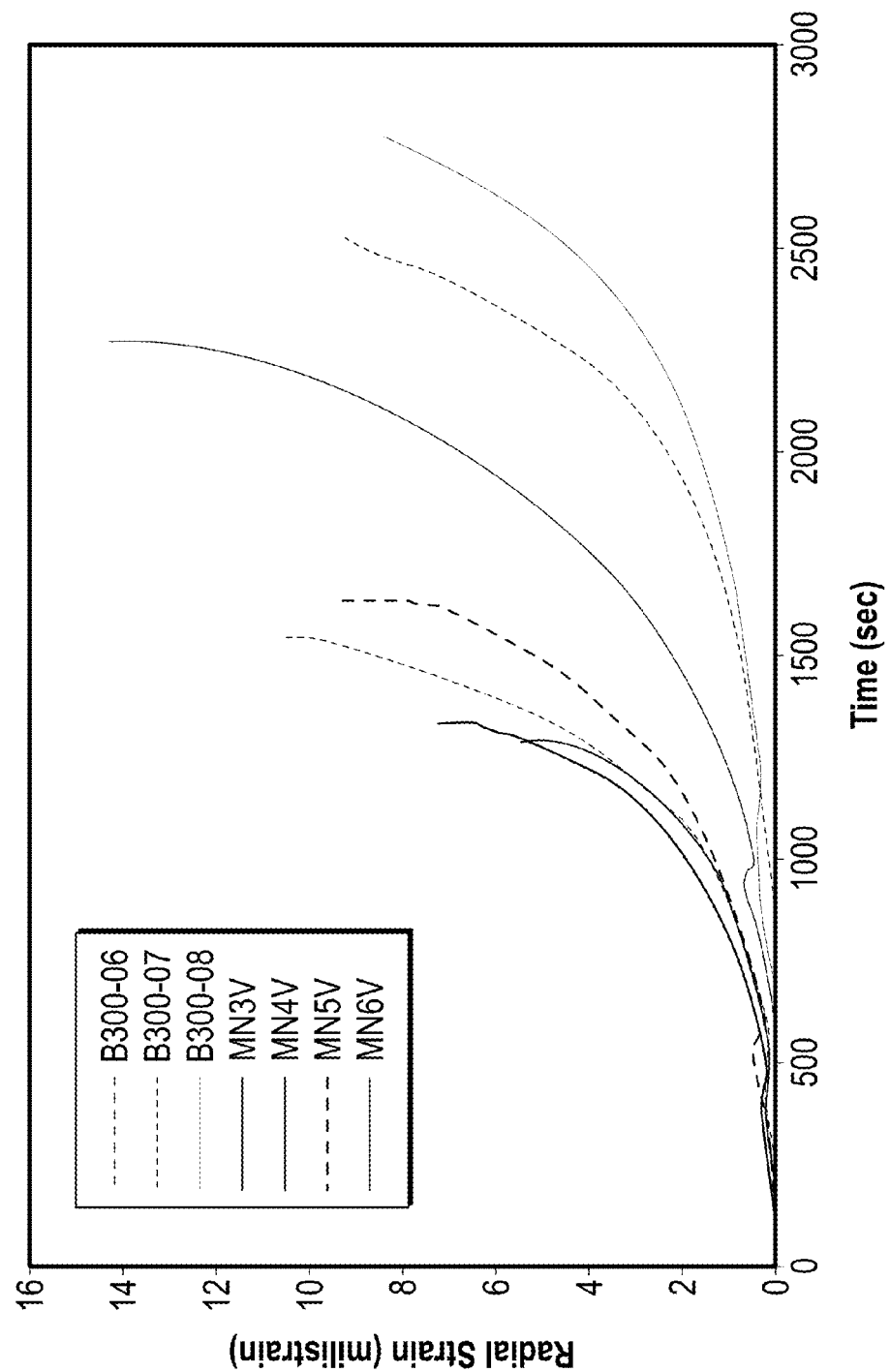
FIG. 5 shows the variation of the absolute value of the radial strain with time for plugs conducted with SST tests.
Figure 6A:
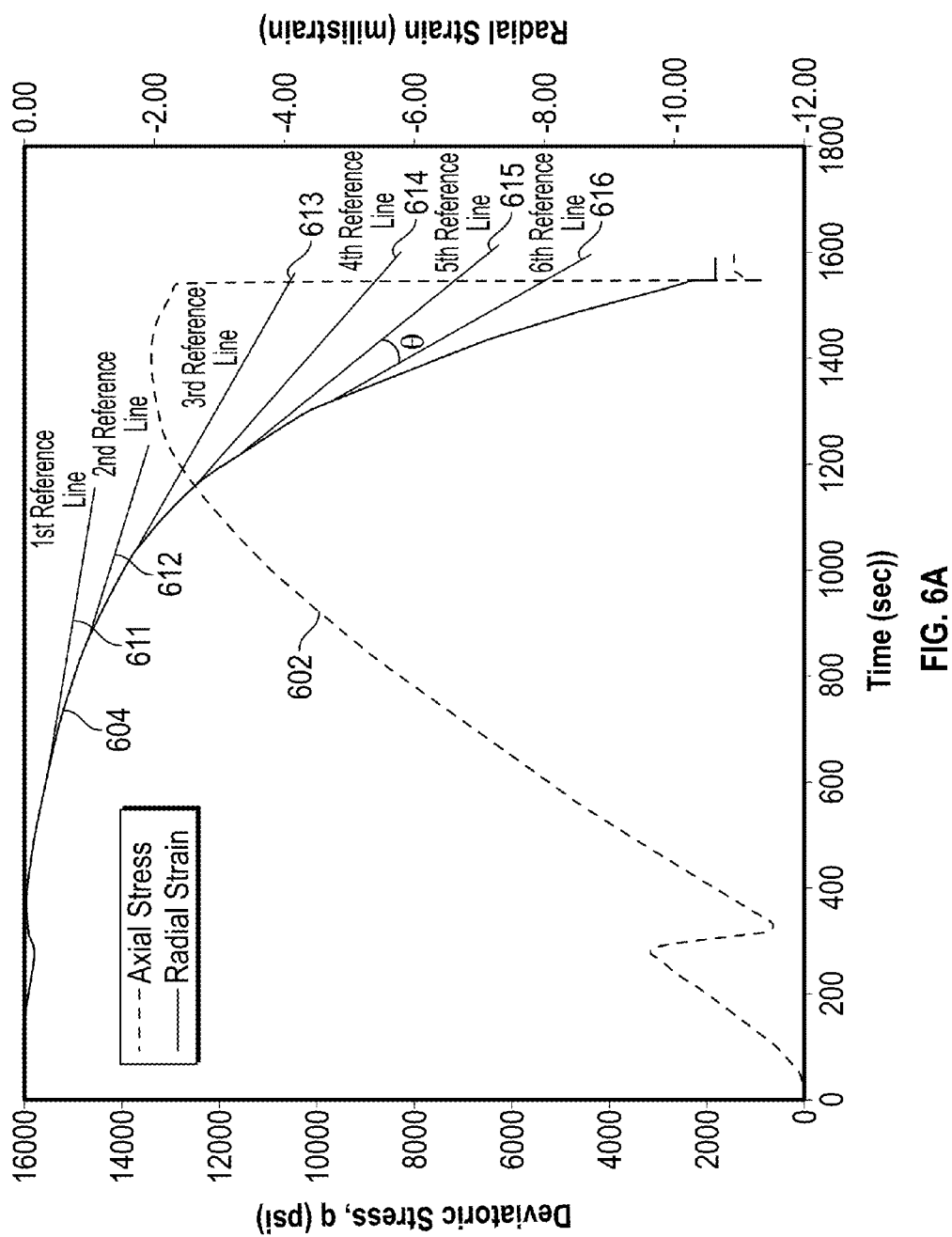
FIGS. 6A-6C plot the variations of the axial stress and the radial strain with respect to time, as well as reference lines tracing the rate of radial strain change.
Figure 6B:
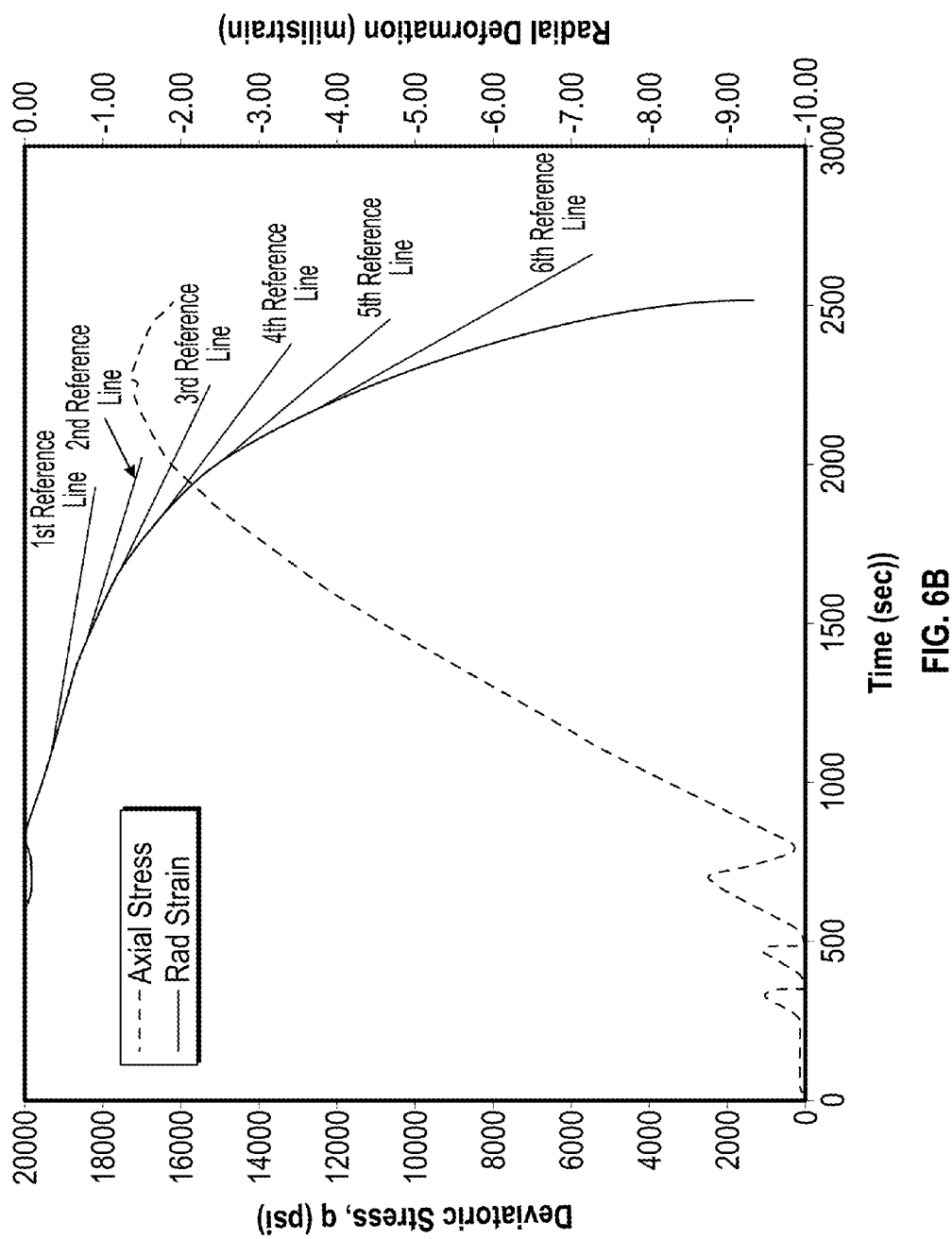
Figure 6C:
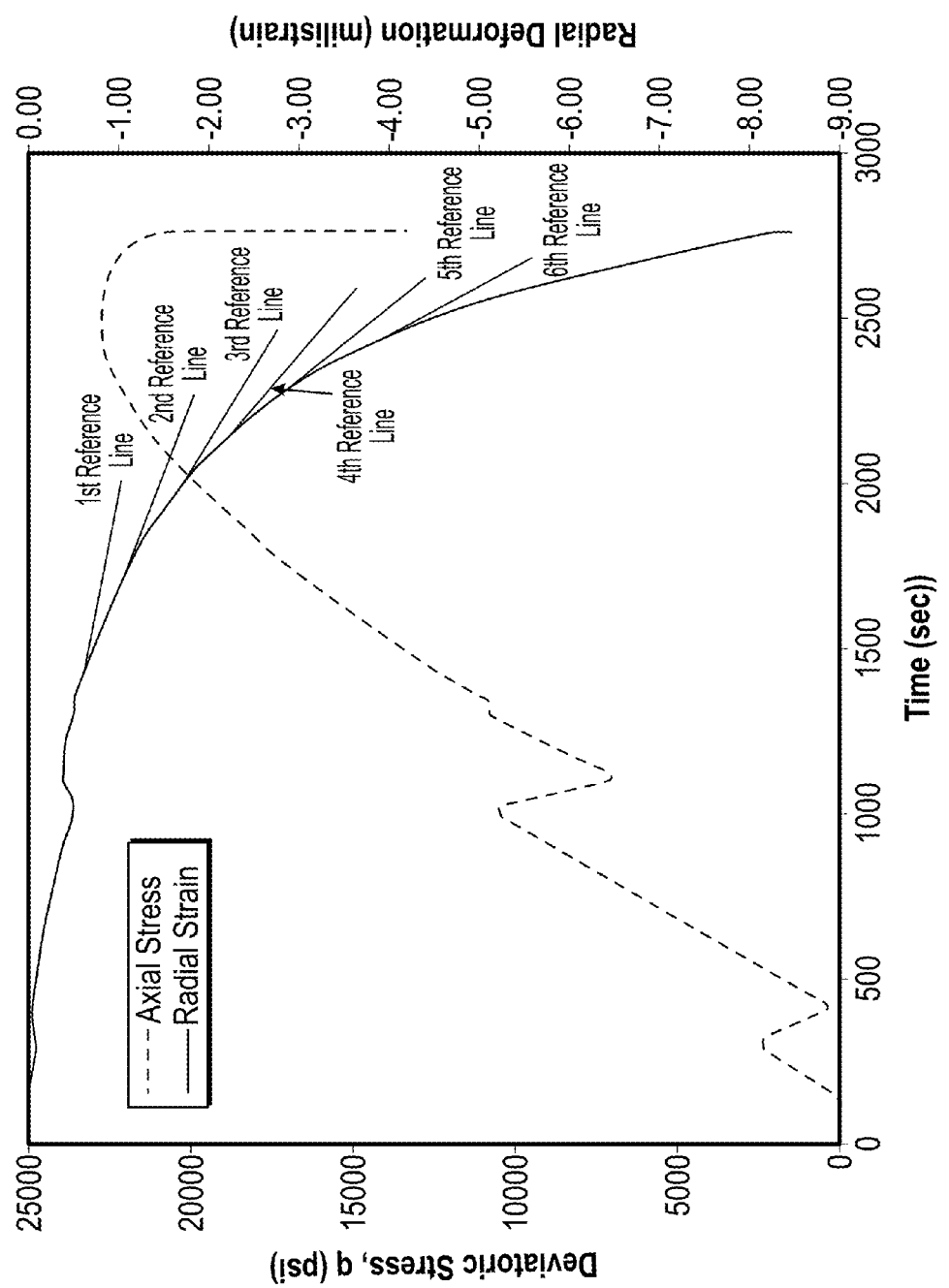
Figure 7A:
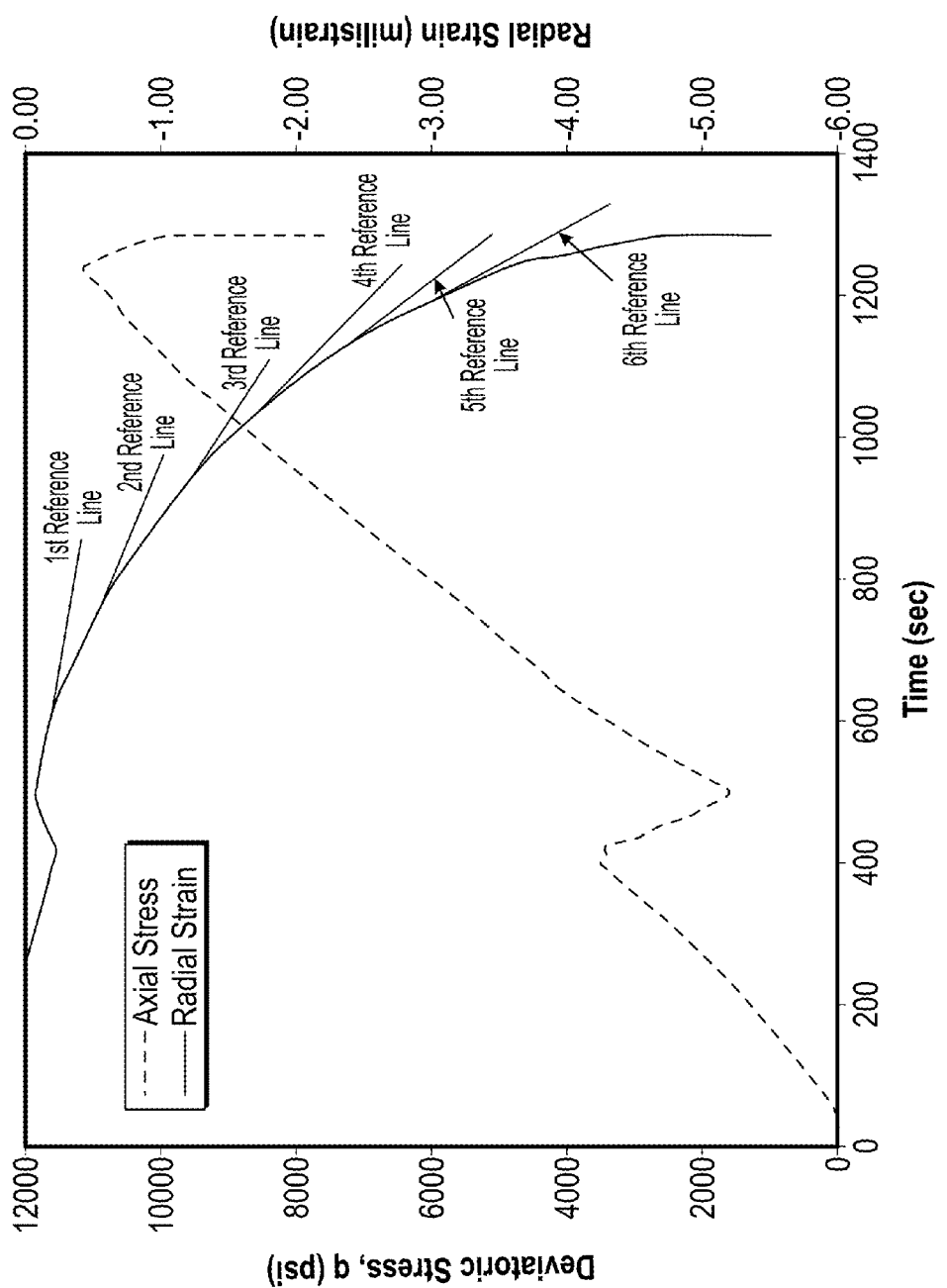
Figure 7B:
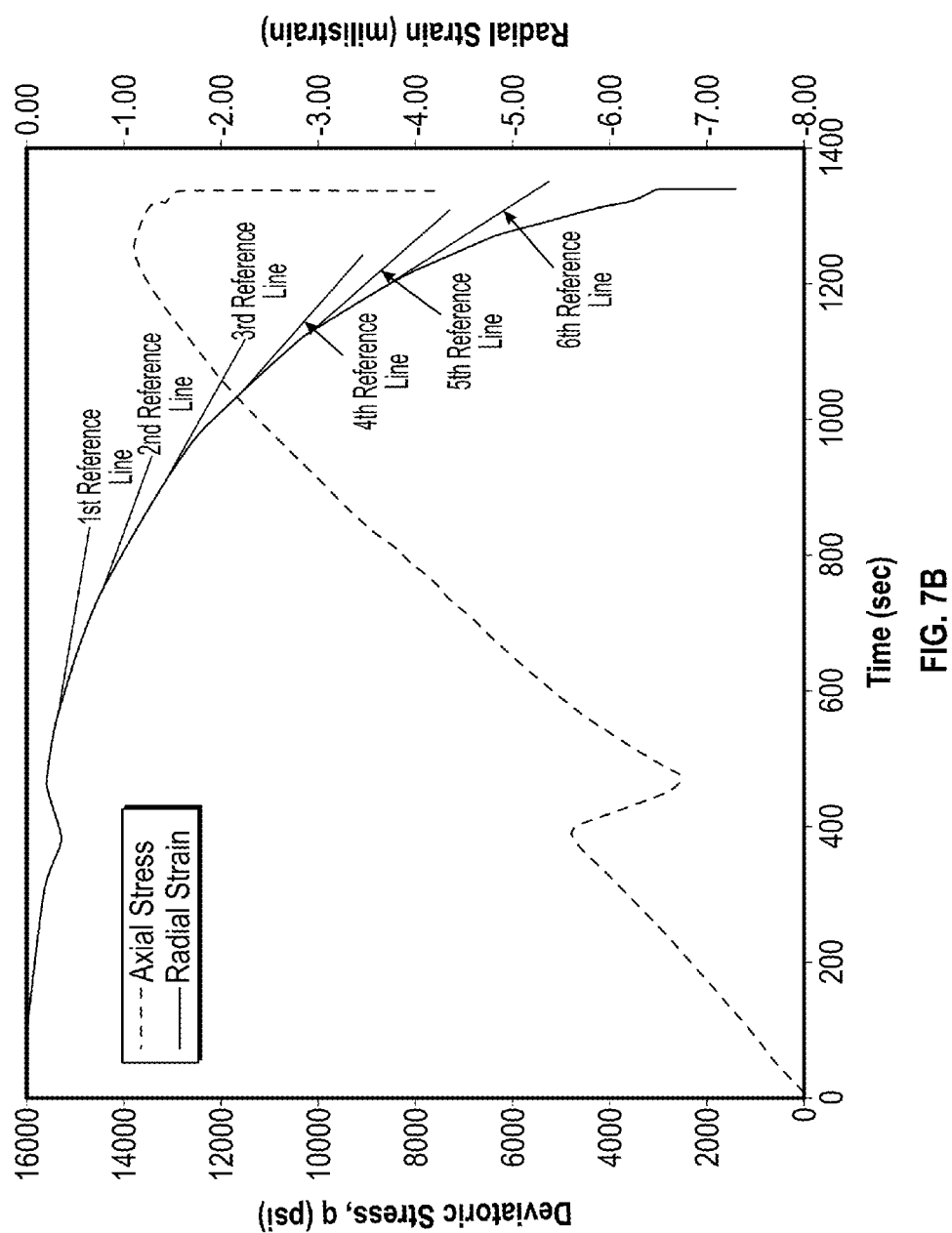
Figure 7C:
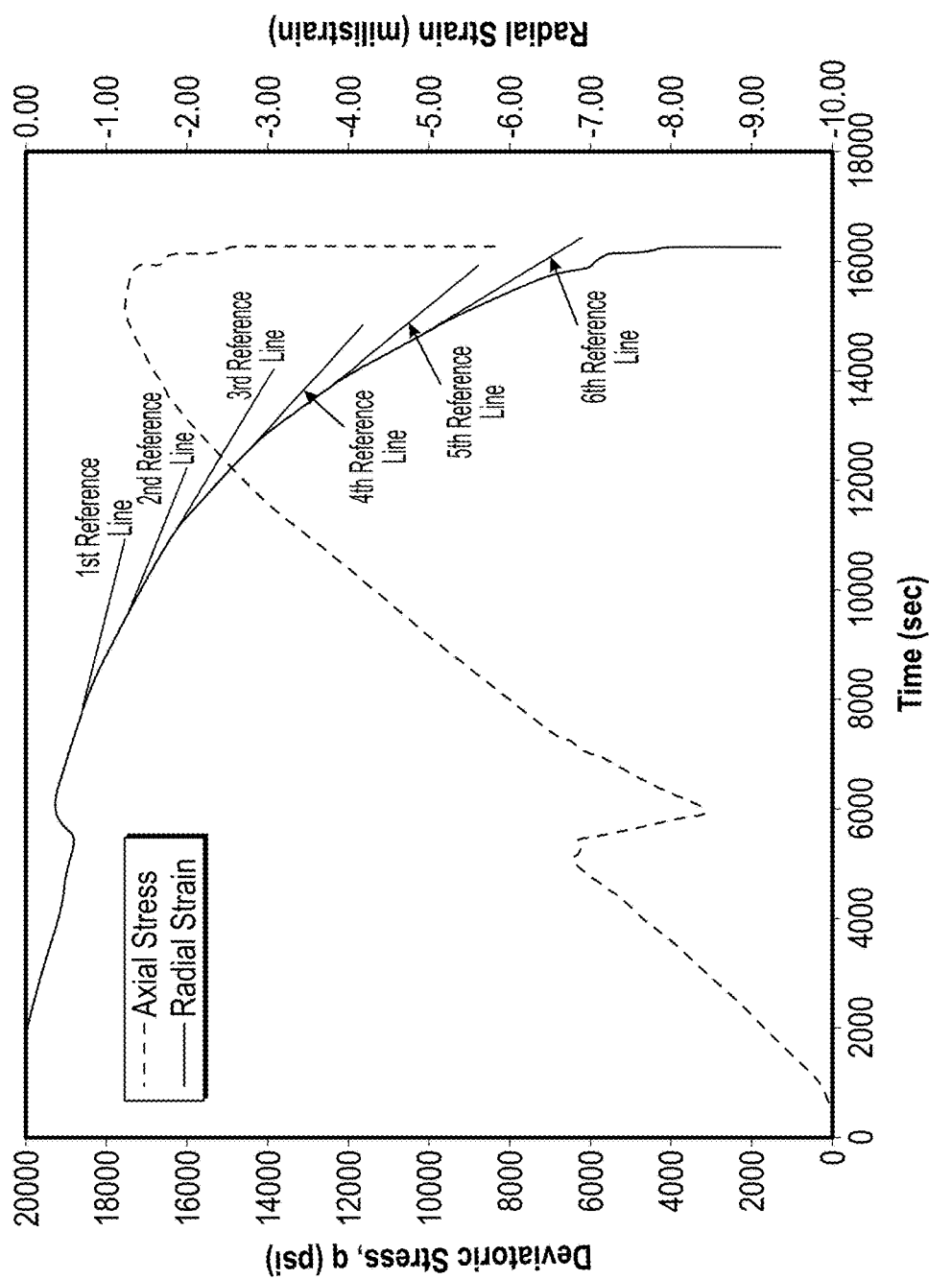
Figure 7D:
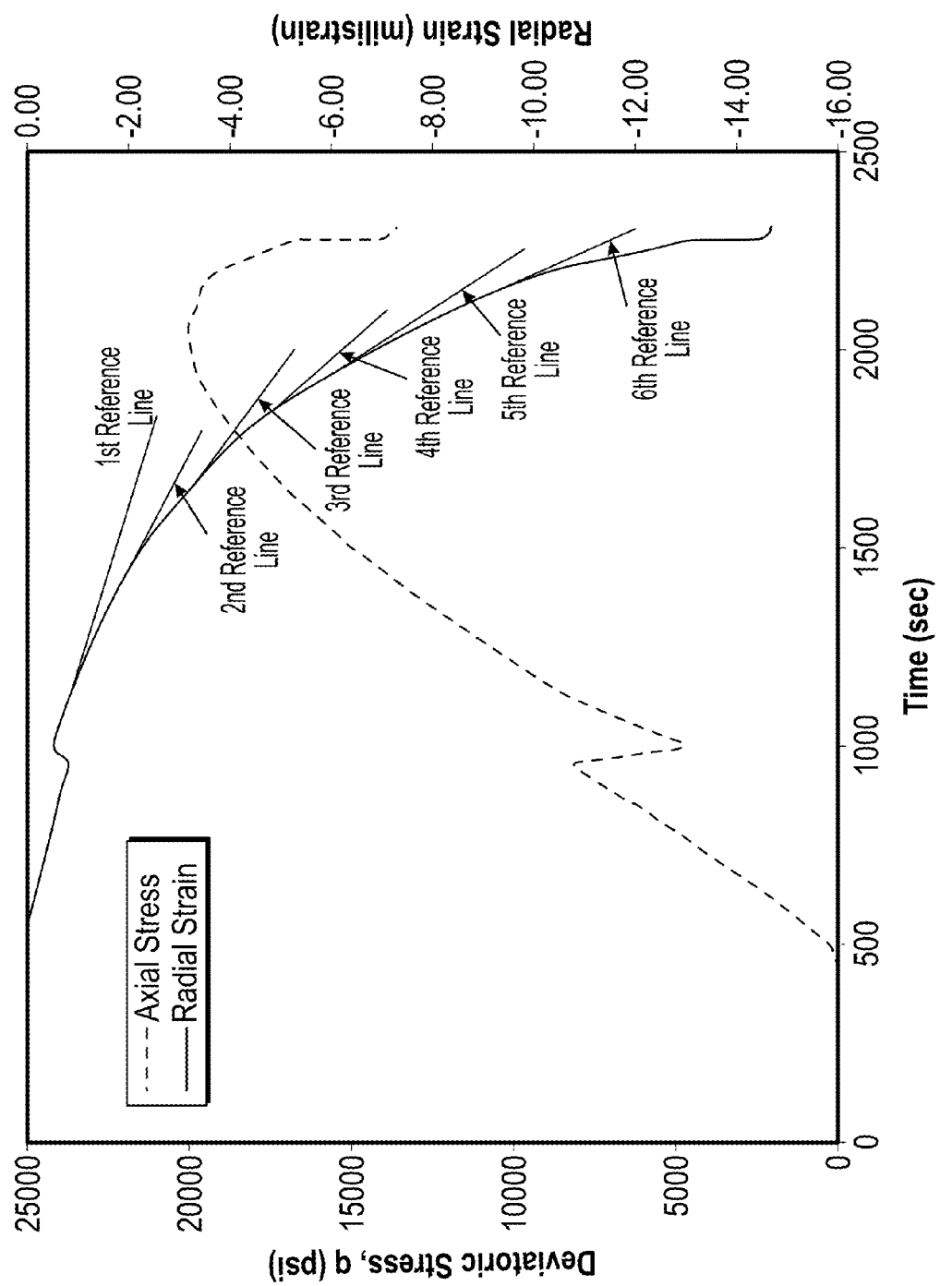

FIG. 5 shows the variation of the absolute value of the radial strain with time for all plugs conducted with the SST tests. It is apparent that the rate of the radial strain change increases exponentially when the plugs reach to the onset of failure during the test.

The techniques of the present disclosure are illustrated in connection with measurement information from a test case using Berea sandstone and Mancos shale plugs in a series of SST and MST tests. Berea sandstone is quite homogeneous; multiple plugs having the same lithofacies were selected.

FIGS. 6A-6C and 7A-7D plot the variations of the axial stress 602 and the radial strain 604 with respect to time, as well as reference lines 611-616 tracing the rate of radial strain change. After the axial loading starts about one minute or when there is enough data on the monitored radial strain curve, a straight line tangent to the radial strain curve is generated manually or automatically, such as the lines in FIG. 6A. This is the first reference line. Once the radial strain curve deviates from the 1st reference line (e.g., the point on the strain curve wherein a threshold deviance is achieved), the 2nd reference line is plotted, which starts from the point where the curve deviates. The deviance may be measured in parameter value or angle from a reference point, such as the beginning of a new line. This process continues until the 4th reference line is generated. At this point, the plug is beyond the elastic zone but still far from the failure. The radial strain curve will deviate from the 4th reference line faster than the previous steps. If the rock is brittle, this is the last reference line that can be drawn before the failure. The stopping point should be the position where the radial strain curve deviates from the reference line at a second deviation threshold (such as a certain angle, e.g., 10 degrees). That is, the state of imminent failure is estimated when the threshold angle is exceeded. If the rock is ductile, a 5th reference line can be drawn. The stopping point is picked when the radial strain curve deviates at a certain threshold angle $\theta$ (e.g., 5 degrees) from the previous reference line. Thus, the threshold angle may be selected according to classification of the rock as brittle or ductile, or more generally, according to known or estimated rock properties. When the stopping point is reached, the axial stress is unloaded to the initial condition. The confining pressure is applied to the value of next stage, and the axial loading begins for next stage. The whole process repeats until all required stages are finished.

Further details of the test case are now presented along with the results. Table 1 lists the various properties of core plugs and their test types. To construct the Mohr-Coulomb failure envelope, three sandstone plugs and four shale plugs were used to conduct the SST tests under various respective confining pressures. For comparison and validation, one plug from each rock type was selected to perform the MST test and derive the corresponding failure envelope.

TABLE 1

Physical properties of core plugs: diameter (D), length (L), bulk density ($\rho_B$).

| Sample | Rock type | Diameter (mm) | Length (mm) | L/D | Bulk density (g/cc) | Test type |
|---|---|---|---|---|---|---|
| B300-06 | Berea sandstone | 37.94 | 74.12 | 1.95 | 2.08 | Single-stage triaxial test |
| B300-07 | Berea sandstone | 38.01 | 77.28 | 2.03 | 2.08 | Single-stage triaxial test |
| B300-08 | Berea sandstone | 37.91 | 76.36 | 2.01 | 2.08 | Single-stage triaxial test |
| B300-15 | Berea sandstone | 38.16 | 74.25 | 1.95 | 2.08 | Multi-stage triaxial test |
| MN3V | Mancos shale | 25.44 | 50.54 | 1.99 | 2.53 | Single-stage triaxial test |
| MN4V | Mancos shale | 25.46 | 50.55 | 1.99 | 2.53 | Single-stage triaxial test |
| MN5V | Mancos shale | 25.46 | 50.32 | 1.98 | 2.53 | Single-stage triaxial test |
| MN6V | Mancos shale | 25.45 | 50.47 | 1.98 | 2.53 | Single-stage triaxial test |
| MN7V | Mancos shale | 25.45 | 50.51 | 1.98 | 2.53 | Multi-stage triaxial test |

All plugs were cut to have a ratio of length to diameter (L/D) equal or close to 2. The end-faces were grinded to the plug parallelism meeting the standard specifications for rock mechanics testing suggested by American Society for Testing and Materials (ASTM, 2004). A rubber jacket with two metals inserted was used to isolate the rock sample from the confining fluid in the pressure cell. The metals were designed to place the radial strain sensor and avoid the rubber deformation with the confining pressure. The plug was placed in the rubber jacket and mounted on the core-holder, where two axial linear variable differential transformers (LVDT) and one radial LVDT were attached to measure the axial and radial strain (See FIG. 3A).

For each SST test, the confining pressure was kept constant during the axial loading. The shear path (axial loading) was servo-controlled by the displacement of the axial piston in the triaxial cell. The loading rate imposed was 2.25 mm per hour. During the axial loading, at least one cycle of unloading and reloading was carried out in the elastic zone for evaluating the elastic properties in the unloading stress path. Table 2 lists the experimental results from SST tests at various confining pressures for Berea sandstone and Mancos shale. Generally, Young's moduli from the loading paths were lower than those from unloading paths, while the opposite is true for Poisson's ratio.

TABLE 2

Results from the SST compressive tests at various confining pressures ($C_p$): peak stress ($q_{max}$), Young's modulus ($E_L$) and Poisson's ration ($v_L$) from loading paths, $E_u$ and $v_u$ from unloading paths.

| Sample | $C_p$ (psi) | $q_{max}$ (psi) | $E_L$ (×10$^6$, psi) | $E_u$ (×10$^6$, psi) | $v_L$ | $v_u$ |
|---|---|---|---|---|---|---|
| B300-06 | 1,501 | 13,408 | 2.57 | 2.96 | 0.32 | 0.11 |
| B300-07 | 2,997 | 17,468 | 2.35 | 3.06 | 0.24 | 0.07 |
| B300-08 | 4,999 | 22,822 | 3.01 | 3.70 | 0.20 | 0.11 |
| MN3V | 216 | 11,093 | 1.18 | 1..92 | 0.25 | 0.09 |
| MN4V | 723 | 13,727 | 1.41 | 2.37 | 0.28 | 0.11 |
| MN5V | 2,174 | 17,684 | 1.58 | 2.54 | 0.24 | 0.12 |
| MN6V | 4,348 | 20,113 | 1.68 | 3.00 | 0.27 | 0.14 |

FIGS. 8A & 8B display the Mohr-Coulomb failure envelopes constructed from the measurements of the SST tests described above. The failure envelope is the best-fit line representing the locus of shear and normal stresses at failure for the rock tested. This envelope delineates stable and unstable states of stress for a given rock material. From FIGS. 8A & 8B, one would predict that for stress states below the failure envelope, the sandstone or Mancos shale would be stable. However, if the stress state yielded shear and normal stresses plotting above the envelope, then such a condition would be unstable and failure would be likely to occur. The failure envelope reveals that the cohesive strength of Berea sandstone is 2,442 psi and its internal friction angle is 35°, while Mancos shale has the cohesive strength of 3,351 psi and the internal friction angle of 31° (Table 5). One also could infer from FIGS. 8A & 8B that the uniaxial or unconfined compressive strength (UCS) of sandstone and shale are 9,384 psi and 11,769 psi, respectively.

Berea sandstone plug B300-15 and Mancos shale plug MN7V (Table 1) were used to test and validate the method described above in the MST test for determining the Mohr-Coulomb failure envelope. Results are compared with those from the SST tests in FIGS. 8A & 8B. Four stages are applied for Berea sandstone plug with the confining pressures of 500, 1500, 3000 and 5000 psi, respectively. For Mancos shale plug, the MST test is performed at three stages of 721, 2173, and 4348 psi, respectively. The last stage continues until the plug fails.

FIGS. 9A-9D show the profiles of radial strain and axial load illustrating results from MST testing of two plugs in accordance with embodiments of the present disclosure. The reference lines 902 are shown on each stage except the last. In implementations of the present disclosure, the curve, the reference lines or other results or formation information may be displayed on a graphic display (e.g., GUI), recorded, or used to conduct further borehole operations. Any or all of these may occur in substantially real time. The plot of axial load may be provided given to visually provide reference of the load applied on the plug in comparison with the previous stages.

For sandstone, the first stage may intentionally be terminated early when the third reference line is established, in order to evaluate the size of the Mohr circle. For the other two stages, the stopping point may be selected when the fourth reference line is generated. For Mancos plug, the first two stages may be terminated when the fourth reference line is shown on the radial strain curve. Tables 3 and 4 list the experimental results from MST tests for Berea sandstone and Mancos shale using these heuristics.

TABLE 3

Results from the MST compressive tests on Berea sandstone plug B300-15 at various confining pressures ($C_p$): peak stress ($q_{max}$), Young's modulus ($E_L$) and Poisson ration ($v_L$) from loading paths, $E_u$ and $v_u$ from unloading paths.

| Stages | $C_p$ (psi) | $q_{max}$ (psi) | $E_L$ (×10$^6$, psi) | $E_u$ (×10$^6$, psi) | $v_L$ | $v_u$ |
|---|---|---|---|---|---|---|
| 1$^{st}$ | 500 | 5,247 | 2.01 | 2.49 | 0.33 | 0.27 |
| 2$^{nd}$ | 1,500 | 11,435 | 2.32 | 2.77 | 0.33 | 0.32 |
| 3$^{rd}$ | 3,000 | 15,467 | 2.51 | 2.89 | 0.32 | 0.31 |
| 4$^{th}$ | 5,000 | 19,591 | 2.46 | — | 0.17 | — |

TABLE 4

Results from the MST compressive tests on Mancos shale plug MN7V at various confining pressures ($C_p$): peak stress ($q_{max}$), Young's modulus ($E_L$) and Poisson ration ($v_L$) from loading paths, $E_u$ and $v_u$ from unloading paths.

| Stages | $C_p$ (psi) | $q_{max}$ (psi) | $E_L$ (×10$^6$, psi) | $E_u$ (×10$^6$, psi) | $v_L$ | $v_u$ |
|---|---|---|---|---|---|---|
| 1$^{st}$ | 721 | 10,584 | 1.31 | 2.74 | 0.27 | 0.13 |
| 2$^{nd}$ | 2,173 | 14,134 | 1.99 | 3.15 | 0.27 | 0.21 |
| 3$^{rd}$ | 4,348 | 19,764 | 2.53 | — | 0.17 | — |

Again, Young's moduli from the unloading paths are higher than those from loading paths for both plugs. Poisson's ratio of sandstone is almost same from both loading and unloading paths, while Mancos shale has a lower value of Poisson's ratio from the unloading paths than those from loading paths.

FIGS. 10A & 10B display the Mohr-Coulomb failure envelopes constructed from the measurements of MST tests on Berea sandstone and Mancos shale. As expected, the Mohr circle of sandstone from the first stage is smaller because this stage was intentionally terminated early. The failure envelope (or the straight line) is perfectly tangent on three Mohr circles constructed from the measurements of the 2nd to 4th stages. For Mancos shale, the failure envelopes can also be derived well from its three-stage measurements. The cohesive strength and the internal friction angle φ of Berea sandstone is derived from the failure envelope, whose values are 2,207 psi and 33°, respectively (Table 5). Their values are very close to those from the SST tests, although they are a little lower. The difference between them is less than 10%, which may be attributable to the intrinsic heterogeneity of the rock.

TABLE 5

Comparison of Mohr-Coulomb parameters between SST and MST tests for Berea sandstone and Mancos shale plugs.

| Parameter | Berea sandstone | | | Mancos shale | | |
|---|---|---|---|---|---|---|
| | Single-stage | Multi-stage | Difference | Single-stage | Multi-stage | Difference |
| $S_o$ | 2,442 | 2,207 | 10% | 3,351 | 2,315 | 31% |
| φ | 35 | 33 | 6% | 31 | 34 | 10% |
| UCS | 9,384 | 8,114 | 14% | 11,769 | 8,706 | 26% |
| μ | 0.7 | 0.65 | 7% | 0.59 | 0.67 | 14% |

For Mancos shale, the cohesive strength derived from the MST test is 2,315 psi—lower than that from the SST tests. Their difference is about 31%. This can be explained as follows: Mancos shale is highly anisotropy and heterogeneous and could be from various areas. The internal friction angle of Mancos shale is almost the same for both the SST tests and MST test.

UCS values derived from the MST tests are 8,114 psi for sandstone and 8,706 psi for Mancos shale, respectively. Both are lower than the values from the SST tests. FIGS. 11A-11B compare the Mohr-Coulomb failure envelopes constructed from the SST and MST tests. The failure envelopes are plotted in the coordinate system of normal stresses $\sigma_1$-$\sigma_2$. The envelope from the MST tests is below that from the SST tests, which may have possible explanations. Multiple plugs used in the SST tests could be different in both structures and mineralogical components. On the other hand, the damage accumulated from the early stages in a MST test can change the structure of the plug and its properties.

As shown above, estimation of the MCFE via the techniques of the present disclosure resulted in no error. Detailed knowledge of mechanical properties of the formation is desirable in the hydrocarbon production business, because these properties can affect the planning of drilling, fracturing, and other operations. Techniques to estimate these properties (and characterize the formation) allow for mitigation or utilization of their cumulative effects.

Core samples are often taken during or after drilling operations. In turn, future drilling operations may be conducted in dependence upon formation information resulting from testing these core samples.

FIG. 12A schematically illustrates a wellbore system 1200 having a downhole tool 110 configured to acquire core samples. The system 1200 may include a conventional derrick 1260 erected on a derrick floor 1270. A conveyance device (carrier 1215) which may be rigid or non-rigid, may be configured to convey the downhole tool 1210 into wellbore 1250 in proximity to formation 1280. The carrier 1215 may be a drill string, coiled tubing, a slickline, an e-line, a wireline, etc. Thus, depending on the configuration, the tool 1210 may be used during drilling and/or after the wellbore 1250 has been formed. While a land system is shown, the teachings of the present disclosure may also be utilized in offshore or subsea applications.

Downhole tool 1210 may be coupled or combined with additional tools e.g., some or all the information processing system described herein. The carrier 1215 may include embedded conductors for power and/or data for providing signal and/or power communication between the surface and downhole equipment (e.g., a seven conductor cable).

The carrier 1215 may include a bottom hole assembly (BHA), which may include a drilling motor for rotating a drill bit. Borehole fluid (e.g., downhole fluid, or drilling fluid) 190 may be present between the formation 1280 and the downhole tool 1210.

A control unit (or controller) may operate the core acquisition tool 1210, or may perform drilling operations, including adjusting drilling parameters or otherwise operating elements of system 1200 (e.g., geosteering) in accordance with formation information resulting from core testing. Control of these components may be carried out using one or more models derived using methods described below.

At least one processor, which may also implement the control unit, may process signal information generated from sensor measurements. The at least one processor may record, transmit, or display (e.g., render on a computer monitor) the information or parameters of interest or models generated using the information. The at least one processor may be implemented at (or may further communicate with further processors at) suitable locations downhole (e.g., on the tool or carrier) at the surface, or remotely. The processor may process data relating to the operations and data from the sensors, and may control one or more downhole operations performed by system. The control unit may be a computer-based unit that may be implemented as a hardware environment, as discussed in greater detail with respect to FIG. 13 below.

FIG. 13 illustrates a hardware environment in accordance with embodiments of the present disclosure. Certain embodiments of the present disclosure may be implemented with a hardware environment 1301 that includes an information processor 1309, an information storage medium 1311, an input device 1313, processor memory 1317, and may include peripheral information storage medium 1319. The hardware environment may be at the surface, in the wellbore, in the tool 1210, at the rig, or at a remote location. Moreover, the several components of the hardware environment may be distributed among those locations. The input device 1313 may be any information reader or user input device, such as data card reader, keyboard, USB port, etc. The information storage medium 1311 stores information provided by sensors on tool 1210. Information storage medium 1311 may be any non-transitory computer information storage device, such as a ROM, USB drive, memory stick, hard disk, removable RAM, EPROMs, EAROMs, EEPROM, flash memories, and optical disks or other commonly used memory storage system known to one of ordinary skill in the art including Internet based storage. Information storage medium 1311 stores a program that when executed causes information processor 1309 to execute the disclosed method. Information storage medium 1311 may also store formation information, or the formation information may be stored in a peripheral information storage medium 1311, which may be any standard computer information storage device, such as a USB drive, memory stick, hard disk, removable RAM, network based storage or other commonly used memory storage system known to one of ordinary skill in the art including Internet based storage.

Hardware environment may be any form of computer or mathematical processing hardware, including Internet based hardware. When the program is loaded from information storage medium 1311 into processor memory 1317 (e.g. computer RAM), the program, when executed, causes information processing device 1311 to retrieve signal information from galvanic TEM measurements from either information storage medium 1311 or peripheral information storage medium 1319 and process the information to estimate a parameter of interest.

In various implementations the control unit may be implemented as at least one processor in a downhole tool, elsewhere in the carrier, at the surface, or remotely. The same or related processor may also be used to automatically control compression testing equipment, such as the system of FIG. 3A, as well as estimate imminent rock failure in the core sample, estimating an MCFE, estimating parameters of interest, and performing other methods in accordance with the present disclosure.

In some embodiments stored data may be used in estimating parameters of interest. These data may be obtained by, for example, retrieving previously acquired data from a data repository, from local memory, or from other associated storage, or may be carried out by retrieving previously calculated or estimated parameters from such storage. In some embodiments, the data may be acquired at the same time as the acquisition of limited aperture log data, while in other instances data may be acquired in separate periods. As one practical example, lithological information or logging information from logs taken in connection with previous operations may be used as a source of data for some of the processes described herein.

Methods embodiments may include conducting further operations in the earth formation in dependence upon the estimated parameter or upon models created using the estimated parameter. Further operations may include at least one of: i) extending the borehole; ii) drilling additional boreholes in the formation; iii) performing additional measurements on the formation; iv) estimating additional parameters of the formation; v) installing equipment in the borehole; vi) evaluating the formation; vii) optimizing present or future development in the formation or in a similar formation; viii) optimizing present or future exploration in the formation or in a similar formation; ix) evaluating the formation; and x) producing one or more hydrocarbons from the formation.

Fracturing operations may be carried out to initiate hydrocarbon production or for purposes of well evaluation. Such operations may use example stimulation embodiments as discussed below. Hydraulic fracture may be produced in the formation by injection of a fracturing fluid in an injection borehole. Predicting propagation of the hydraulic fracture may be carried out using analysis as described below.

Propagation of the hydraulic fracture may be predicted by modeling the earth formation (e.g., using a three-dimensional geomechanical model) and using parameters such as the MCFE of associated core samples as an input. Stresses acting on the formation and fracture flow properties may be incorporated into a time-based (e.g., incremental) flow simulation. Alternatively, propagation may be predicted using a special purpose-built heuristic, using a neural network (with the principal direction of the far-field stress as one of the inputs), and so on. The predicted fracture may then be used alone or as part of a larger simulation (e.g., as a constraint) in planning further operations associated with the borehole or the formation. In some aspects, the hydraulic fracture may be predicted.

Predicting the propagation of the hydraulic fracture enables optimization of the fracture, along with optimization and project planning of other related future operations in the borehole, the formation, or related formations. Accurate propagation prediction enables proper orientation of horizontal laterals to minimize breakdown pressure, maximize fracture connectivity in the near-wellbore, and create an ideal geometry for maximum coverage of the intervals between wells by the hydraulic fracture and accompanying stimulated rock volume.

FIG. 14 illustrates a stimulation system in accordance with embodiments of the present disclosure. The system 1403 includes a downhole tool string 1410, such as a stimulation string, wireline, or other carrier conveyed in a borehole 1440 surrounded by casing 1418. In one embodiment, the system 1403 is configured as a hydraulic stimulation system, but may also configured for additional functions such as hydrocarbon production, evaluation of the formation, evaluation of the borehole, and so on. As described herein, "stimulation" may include any injection of a fluid into a formation. An exemplary stimulation system may be configured as a cased or open hole system for initiating fractures and/or stimulating existing fractures in the formation. A fluid may be any flowable substance.

The tool string 1410 may include one or more tools or components to facilitate stimulation of the formation 1480. For example, the tool string 1410 may include a fracturing assembly 1420 including, e.g., injection nozzles and mechanical valve devices (e.g., fracturing sleeves, drop-ball devices, and so on). The tool string 1410 may include a perforation assembly 1422. The tool string 1410 may include additional components, such as one or more isolation components 1424 (e.g., packer subs, frangible barriers, etc.). Subs may include one or more processors or associated electronics configured to communicate with a surface processing unit and/or control the respective component or assembly. The system 1403 may be a hydraulic fracturing system that includes an injection device 1430 (e.g., a high pressure pump) in fluid communication with a fluid source 1450. The injection device 130 injects fluid into the string 1410 to introduce fluid into the formation 1480. Measurement and control devices, including one or more sensors responsive to pumping parameters, may be included for monitoring and control of the respective operation (e.g., hydraulic fracturing or other stimulation).

As used above, an information processing device is any device that transmits, receives, manipulates, converts, calculates, modulates, transposes, carries, stores, or otherwise utilizes information. In several non-limiting aspects of the disclosure, an information processing device includes a computer that executes programmed instructions for performing various methods. Herein, the term "information" may include one or more of: raw data, processed data, and signals.

The term "carrier" as used above means any device, device component, combination of devices, media and/or member that may be used to convey, house, support, or otherwise facilitate the use of another device, device component, combination of devices, media and/or member. Exemplary non-limiting carriers include drill strings of the coiled tube type, of the jointed pipe type, and any combination or portion thereof. Other carrier examples include casing pipes, wirelines, wireline sondes, slickline sondes, drop shots, downhole subs, bottom hole assemblies, drill string inserts, modules, internal housings, and substrate portions thereof.

The tool 1210 may also include sensors, tools, or instruments configured to: (i) actively or passively collect information about the various characteristics of the formation, (ii) provide information about tool orientation and direction of movement, (iii) provide information about the characteristics of the reservoir fluid and/or (iv) evaluate reservoir conditions (e.g., formation pressure, wellbore pressure, temperature, etc.). Exemplary devices may include resistivity sensors (for determining the formation resistivity, dielectric constant and the presence or absence of hydrocarbons), acoustic sensors (for determining the acoustic porosity of the formation and the bed boundary in the formation), nuclear sensors (for determining the formation density, nuclear porosity and certain rock characteristics), and nuclear magnetic resonance sensors (for determining the porosity and other petrophysical characteristics of the formation). Other exemplary devices may include gyroscopes, magnetometers, and sensors that collect formation fluid samples and determine the characteristics of the formation fluid, which include physical characteristics and chemical characteristics.

In some embodiments, the borehole may be utilized to recover hydrocarbons. In other embodiments, the borehole may be used for geothermal applications, water production, mining, tunnel construction, or other uses.

The term "information" as used herein includes any form of information (analog, digital, EM, printed, etc.). As used herein, a processor is any information processing device that transmits, receives, manipulates, converts, calculates, modulates, transposes, carries, stores, or otherwise utilizes information. In several non-limiting aspects of the disclosure, a processor includes a computer that executes programmed instructions for performing various methods. These instructions may provide for equipment operation, control, data collection and analysis and other functions in addition to the functions described in this disclosure. The processor may execute instructions stored in computer memory accessible to the processor, or may employ logic implemented as field-programmable gate arrays ('FPGAs'), application-specific integrated circuits ('ASICs'), other combinatorial or sequential logic hardware, and so on.

Thus, configuration of the processor may include operative connection with resident memory and peripherals for executing programmed instructions. In some embodiments, estimation of the parameter of interest may involve applying a model. The model may include, but is not limited to, (i) a mathematical equation, (ii) an algorithm, (iii) a database of associated parameters, or a combination thereof. "Profile" as used herein refers to a model. The term "substantially deviating," as used herein refers to deviation more significant than would be expected from mere noise, such as, for example, deviation representative of more than a threshold angle of a reference line (e.g., tangent to the curve at that point) from a previous reference line, wherein the threshold angle may be 1 percent, 2 percent, 3 percent, 4 percent, 5 percent, 7.5 percent, or 10 percent or more.

In a typical operation, core samples may be obtained by extracting a core (which may be cylindrical in shape) of a particular or customary diameter and cutting a conventional length from that core. This may be known as a bulk sample. A plug sample may be taken from the bulk sample and subjected to mechanical testing. Use of the term "core sample" herein refers to any of these objects (core, bulk sample, plug sample, and so on), although plug samples may be convenient for use with typical instruments currently available. The state of imminent rock failure is achieved immediately before this breaking point. Immediately before, as used herein, refers to a point having substantially the same stress parameter values as failure without occurrence of the state of failure. "Substantially the same" refers to values within deviations such as to not effect further operations.

Estimated parameters of interest may be stored (recorded) as information or visually depicted on a display. Aspects of the present disclosure relate to modeling a volume of an earth formation using the estimated parameter of interest, such as, for example, by associating estimated parameter values with portions of the volume of interest to which they correspond. The model of the earth formation generated and maintained in aspects of the disclosure may be implemented as a representation of the earth formation stored as information. The information (e.g., data) may be stored on a non-transitory machine-readable medium, and rendered (e.g., visually depicted) on a display.

Control of components of apparatus and systems described herein may be carried out using one or more models as described above. For example, at least one processor may be configured to modify operations i) autonomously upon triggering conditions, ii) in response to operator commands, or iii) combinations of these. Such modifications may include changing drilling parameters, steering the drillbit (e.g., geosteering), changing a mud program, optimizing measurements, and so on. Control of these devices, and of the various processes of the drilling system generally, may be carried out in a completely automated fashion or through interaction with personnel via notifications, graphical representations, user interfaces and the like. Reference information accessible to the processor may also be used.

The processing of the measurements by a processor may occur at the tool, or at a remote location. The data acquisition may be controlled at least in part by the electronics. Implicit in the control and processing of the data is the use of a computer program on a suitable non-transitory machine readable-medium that enables the processors to perform the control and processing. The non-transitory machine-readable medium may include ROMs, EPROMs, EEPROMs, flash memories and optical disks. The term processor is intended to include devices such as a field programmable gate array (FPGA).

The terms "line," "curve," "point," and "tangent" refer to mathematical relationships between a collection of parameter values which can easily be understood as graphical expressions. However, graphical display of the concepts described herein is not required. For example, analog or digital signal processing may be employed using various algorithms to carry out steps described herein electronically, and without display, such as, for example, generating reference lines and identifying portions of a curve substantially deviating from the reference line.

In another embodiment, the determination of imminent rock failure state may performed during a rock compression test by employing a quantitative method, which uses the radial strain gradient (RSG) or radial strain rate (RSR) recorded in real time RSG or RSR is defined as the ratio of the change of radial strain ($\Delta\varepsilon_r$) to the change of time ($\Delta t$) with some mathematical transformation applied.

$$RSG = \text{function}\left(\frac{\Delta\varepsilon_r}{\Delta t}, \text{tranformation}\right)$$

RSG is recorded in real time during the rock compression test, therefore informing the operator to prepare the stress unloading when reaching at a given or pre-determined critical RSG value. The critical RSG value (defining the imminent rock failure state) can be given or pre-determined from the single-stage triaxial test (SST) or unconfined compression test (UCS)

Software may be employed to calculate automatically the RSG from the measured radial strain.

The RSG method is irrespective of the confining pressure applied on the rock sample and rock type.

The RSG method can be applied on SST, UCS, MST and/or any other compression tests if the radial strain is measured. The idea of RSG approach can also be applied and/or implemented on the acoustic emission count.

Turning now to FIGS. 15, 16, and 17; these figures show the results from a single-stage triaxial test (SST) of a sandstone rock sample. FIGS. 15, 16 and 17 show the data for SST tests at confining pressure of 2000, 4000 and 7000 psi, respectively. For all the three tests the shear failure occurs beyond a peak stress. Irrespective of confining pressure, all the three samples fail at a radial strain gradient of ~90°. During a MST test a good unloading point would be at a stress value just before the peak stress is reached (Highlighted with dotted red line—$\sigma_{RSG}$). A radial strain gradient value of 87° is applicable to all the three confining conditions as an appropriate unloading criteria as being the point of imminent failure. These examples could have been performed using acoustic emission counts as well.

While the foregoing disclosure is directed to specific embodiments of the present disclosure, various modifications will be apparent to those skilled in the art. It is intended that all variations within the scope of the appended claims be embraced by the foregoing disclosure.

What is claimed is:

1. A method for evaluating a core sample obtained from a subterranean earth formation, the method comprising:
  applying a stress to a core sample obtained in the formation;
  taking a plurality of measurements of at least one stress parameter of the core sample over time responsive to the applied stress;
  calculating a rate of change between the plurality of measurements;
  determining a point of imminent failure, wherein the core sample has substantially the same stress parameter values as at failure without occurrence of the state of failure, by:
    applying a transformation to the rate of change to get a transformed rate of change; and
    estimating the point of imminent failure upon the transformed rate of change reaching a threshold value;
  causing applied stress to be ceased upon estimating the imminent rock failure.

2. The method of claim 1 wherein the at least one stress parameter comprises at least one of: i) radial strain with time; and ii) acoustic emission counts with time.

3. The method of claim 1 wherein the transformation comprises dividing the rate by 106.

4. The method of claim 1 comprising using the measurements to determine a Mohr-Coulomb failure envelope for the core sample.

5. The method of claim 1 comprising using the measurements to determine at least one of: i) a parameter of interest of the core sample; and ii) a parameter of interest of the formation.

6. The method of claim 1 comprising determining the threshold value of a transformed rate of change from the core sample over time responsive to an applied stress to the failure in the core sample.

7. A method for evaluating a core sample obtained from a subterranean earth formation, the method comprising:
  modeling a point of imminent failure of the core sample by:

calculating a rate of change between a plurality of measurements of at least one stress parameter of the core sample over time responsive to an applied stress; and determining the point of imminent failure using the rate of change in the plurality of measurements of the at least one stress parameter by:

applying a transformation to the rate of change to get a transformed rate of change; and estimating the point of imminent failure upon the transformed rate of change reaching a threshold value.

* * * * *

UNITED STATES PATENT AND TRADEMARK OFFICE
CERTIFICATE OF CORRECTION

PATENT NO.        : 10,385,687 B2
APPLICATION NO.   : 15/804505
DATED             : August 20, 2019
INVENTOR(S)       : Syed Shujath Ali, Ali Al Dhamen and Guodong Jin Page 1 of 1

It is certified that error appears in the above-identified patent and that said Letters Patent is hereby corrected as shown below:

On the Title Page

Column 1 (72), after Guodong Jin, Katy, TX, add the following inventor -- Bilal Saad, Dhahran City (SA) --

Signed and Sealed this
Second Day of June, 2020

Andrei Iancu
*Director of the United States Patent and Trademark Office*